(12) United States Patent  (10) Patent No.: US 7,043,296 B1
Kasai et al.  (45) Date of Patent: May 9, 2006

(54) BIOELECTRIC SIGNAL DETECTOR AND MASSAGE MACHINE

(75) Inventors: Eiji Kasai, Kyoto (JP); Ryo Fukui, Kyoto (JP)

(73) Assignee: Omron Corporation, Kyoto (JP)

( * ) Notice: Subject to any disclaimer, the term of this patent is extended or adjusted under 35 U.S.C. 154(b) by 290 days.

(21) Appl. No.: 10/130,526

(22) PCT Filed: Nov. 17, 2000

(86) PCT No.: PCT/JP00/08149

§ 371 (c)(1),
(2), (4) Date: May 17, 2002

(87) PCT Pub. No.: WO01/37729

PCT Pub. Date: May 31, 2001

(30) Foreign Application Priority Data

Nov. 19, 1999 (JP) ................................. 11/329063

(51) Int. Cl.
*A61B 5/05* (2006.01)
(52) U.S. Cl. ..................................... 600/547
(58) Field of Classification Search ................. 600/547
See application file for complete search history.

(56) References Cited

U.S. PATENT DOCUMENTS

| 4,033,332 A | * | 7/1977 | Hardway et al. | ........... 600/535 |
|---|---|---|---|---|
| 4,503,863 A | * | 3/1985 | Katims | ........................ 600/554 |
| 4,633,879 A | * | 1/1987 | Ong | ............................ 600/391 |
| 5,724,024 A | | 3/1998 | Sonderegger et al. | ........ 340/562 |
| 6,030,347 A | | 2/2000 | Nakamura et al. | ........... 600/552 |
| 6,265,978 B1 | * | 7/2001 | Atlas | ........................ 340/575 |

FOREIGN PATENT DOCUMENTS

| JP | 46-6994 | | 12/1971 |
|---|---|---|---|
| JP | 52-39983 | | 3/1977 |
| JP | 8-24232 | | 1/1996 |
| JP | 2-248284 | | 9/1997 |
| JP | 10-15011 | * | 1/1998 |
| WO | 95/00368 | | 1/1995 |
| WO | 97/24976 | | 7/1997 |

* cited by examiner

*Primary Examiner*—Eric F. Winakur
(74) *Attorney, Agent, or Firm*—Morrison & Foerster LLP

(57) ABSTRACT

A biosignal sensing device (2) includes an electrode section (12) including a pair of electrodes (12a,12b) mounted so that a living body can be in close proximity to or in contact with the electrodes. An oscillation section (11) supplies a high frequency signal to the electrodes. A reflected-wave level from the electrodes receiving the high frequency signal changes according to a change in impedance in the electrodes that are in close proximity to or in contact with the living body. This change in reflected-wave level reflects a change in impedance resulting from body movement of the living body such as respiration and pulsation. A sensing section (13) senses a signal indicating the change in reflected-wave level. Based on this signal, a signal amplifying section (14) calculates a desired biosignal such as pulse rate and respiration rate.

25 Claims, 23 Drawing Sheets

INPUT WAVEFORM

COMPARISON VOLTAGE

OUTPUT

BIOELECTRIC SIGNAL DETECTOR AND MASSAGE MACHINE

TECHNICAL FIELD

The present invention relates to a biosignal sensing device and a massaging machine using the same. More particularly, the present invention relates to a biosignal sensing device for sensing a biosignal such as pulse rate and respiration rate of a living body such as human body, and a massaging machine using such a biosignal sensing device.

BACKGROUND ART

Various sensors such as optical sensor, capacitance-type sensor and pressure sensor are used as means for sensing the pulse rate and the respiration rate of a living body such as human body. At present, the optical sensor is most commonly used.

The conventional massaging machines merely conduct massaging operation according to a predetermined program. In recent years, however, a massaging machine programmed to sense a biosignal such as pulse rate and respiration rate of a user to be massaged and to conduct massaging operation, i.e., treatment, according to the sensing result is used in practical applications.

Conventionally, however, a sensor of the above type must be attached somewhere on the user's body in order to detect the pulse rate and the respiration rate of the human body. Accordingly, the human body is placed under restraint in some way, which is extremely bothersome in use.

A massaging machine has been developed which is capable of detecting the above biosignal by merely requiring the user to sit on the massaging machine without using a sensor that restrains the human body. For example, such a massaging machine is disclosed in Japanese Laid-Open Publication No. 9-248284.

A conventional chair-type massaging machine of this type uses an optical sensor. The optical sensor is formed from a flexible optical fiber having its one end connected to a light-emitting portion and the other end connected to a light-receiving portion, and the optical fiber is used in contact with the human body.

More specifically, the optical fiber in contact with the human body is bent by slight movement of the human body like pulsation, respiration and the like, thereby varying the quantity of light transmitted from the light-emitting portion to the light-receiving portion through the optical fiber. A biosignal such as pulse rate and respiration rate can be obtained by sensing such variation in light quantity.

The above conventional chair-type massaging machine has such a mechanical structure that the user's weight is intensively placed on one part of the seat surface of the massaging machine when the user is seated thereon. The optical sensor is mounted so that a part of the optical fiber contacts that part. This massaging machine thus detects variation in light quantity caused by deformation of the optical fiber resulting from the body movement of the user, and filters the detection signal to extract a desired biosignal such as pulse rate and respiration rate.

However, the conventional chair-type massaging machine using such an optical sensor has a complicated mechanical structure for transmitting the body movement of the user intensively to the optical fiber, resulting in increased manufacturing costs.

Moreover, extracting the pulse rate and the respiration rate, i.e., physical movement of the human body (mixture of vertical and horizontal movements), by filtering is sometimes difficult in terms of signal processing. Therefore, biosignal detection based on variation in light quantity is problematic in terms of detection accuracy.

It is an object of the present invention to provide a biosignal sensing device capable of accurately sensing a biosignal such as pulse rate and respiration rate without restraining a living body.

It is another object of the present invention to provide a massaging machine incorporating such a biosignal sensing device and thus having a simplified structure and suppressing increase in manufacturing costs.

It is still another object of the present invention to provide a massaging machine incorporating such a biosignal sensing device and thus capable of providing treatment based on a biosignal detected with high accuracy.

DISCLOSURE OF THE INVENTION

The present invention relates to a biosignal sensing device for sensing a biosignal from a living body as a subject, and includes an oscillating section, an electrode section, a sensing section, a signal amplifying section, and a signal processing section. The oscillating section supplies a high frequency signal. The electrode section includes an electrode mounted so that the living body as a subject can be in close proximity to or in contact with the electrode, and the electrode is coupled to receive the high frequency signal from the oscillating section. The sensing section senses a change in impedance that occurs in the electrode receiving the high frequency signal when the living body as a subject is in close proximity to or in contact with the electrode. The signal amplifying section has a filter function to extract a signal according a desired biosignal from a signal corresponding to the sensed change in impedance. The signal processing section produces the desired biosignal from the signal extracted by the signal amplifying section. The sensing section produces and supplies a signal indicating a change in reflected-wave level of the high frequency signal corresponding to the change in impedance that occurs in the electrode according to body movement of the living body. A frequency of the high frequency signal supplied from the oscillating section is preset to a value in a region where the reflected-wave level changes at a high rate according to change in the frequency.

The biosignal sensing device of the present invention obtains a biosignal by sensing a change in impedance that is caused by the body movement at the electrode mounted so that the subject can be in close proximity to or in contact with the electrode. As a result, a biosignal such as pulse rate and respiration rate can be sensed accurately without restraining the living body.

The present invention relates to a massaging machine for giving treatment to a user in an automated manner based on a prescribed program, and includes a massaging unit, a biosignal sensing device, and an operation control section. The massaging unit gives treatment to the user. The biosignal sensing device senses a biosignal from the user. The operation control section drives the massaging unit according to the prescribed program and the sensed biosignal. The biosignal sensing device includes an oscillating section, an electrode section, a sensing section, a signal amplifying section, and a signal processing section. The oscillating section supplies a high frequency signal. The electrode section includes an electrode mounted so that the user can be in close proximity to or in contact with the electrode, and the electrode is coupled to receive the high frequency signal from the oscillating section. The sensing section senses a change in impedance that occurs in the electrode receiving the high frequency signal when the user is in close proximity to or in contact with the electrode. The signal amplifying section has a filter function to extract a signal according to a desired biosignal from a signal corresponding to the sensed change in impedance. The signal processing section produces the desired biosignal from the signal extracted by the signal amplifying section. The sensing section produces and supplies a signal indicating a change in reflected-wave level of the high frequency signal corresponding to the change in impedance that occurs in the electrode according to body movement of the user. A frequency of the high frequency signal supplied from the oscillating section is preset to a value in a region where the reflected-wave level changes at a high rate according to change in the frequency.

The massaging machine of the present invention incorporates the biosignal sensing device that obtains a biosignal by sensing a change in impedance that is caused by the body movement at the electrode mounted so that the user can be in close proximity to or in contact with the electrode. As a result, treatment based on an accurately sensed biosignal can be provided with a simplified, inexpensive structure.

BEST MODE FOR CARRYING OUT THE INVENTION

[Overall Structure of Massaging Machine of the Invention]

Figure 1:
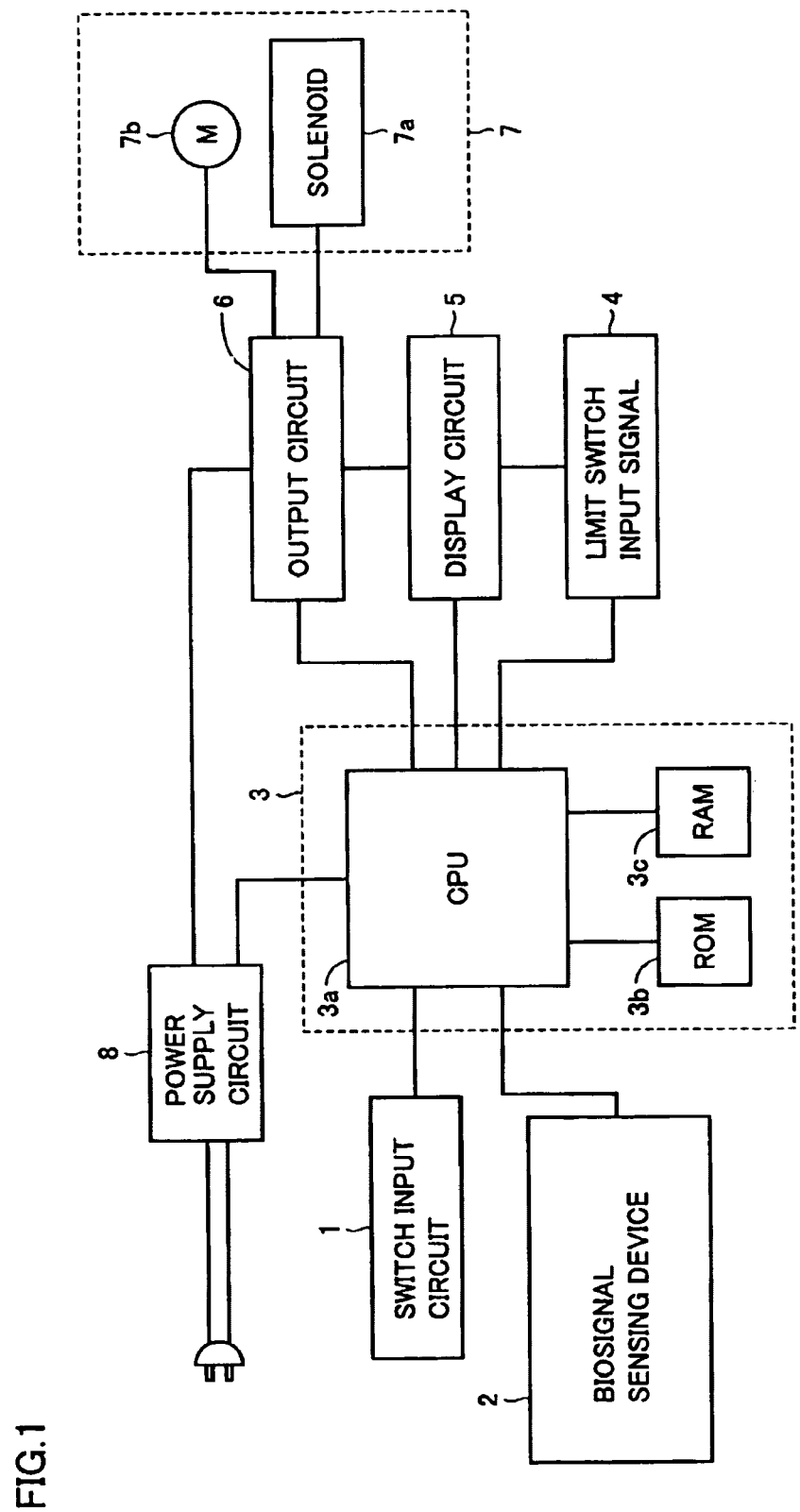
FIG. 1 is a schematic block diagram showing the electrical structure of a massaging machine to which a biosignal sensing device of the present invention is applied.

FIG. 1 is a schematic block diagram showing the electrical structure of a massaging machine to which a biosignal sensing device of the present invention is applied.

Referring to FIG. 1, this massaging machine mainly includes a switch input circuit 1, a biosignal sensing device 2, an operation control section 3, a limit switch input circuit 4, a display circuit 5, an output circuit 6, a massaging unit 7, and a power supply circuit 8.

The operation control section 3 includes a central processing unit (CPU) 3a, a read only memory (ROM) 3b, and a random access memory (RAM) 3c. The massaging unit 7 is mounted in, e.g., the backrest of a chair-type massaging machine, and includes a solenoid 7a and a motor 7b.

Although not shown in the figure, the switch input circuit 1 includes, in addition to a power switch, key switches for designating various operations of the massaging unit 7 such as kneading, tapping, going up and going down.

The biosignal sensing device 2 is a device based on novel detection principles according to the present invention, and produces a biosignal such as pulse rate and respiration rate for output to the CPU 3a of the operation control section 3. The biosignal sensing device 2 will be described in detail below.

For use, the user first turns on the not-shown power switch of the switch input circuit 1, and the CPU 3a then responsively activates the power supply circuit 8, whereby the power supply circuit 8 supplies the power to each part of the massaging machine.

According to the user's designation through the switch input circuit 1, the CPU 3a generates a signal for driving the massaging unit 7 for output to the output circuit 6. In response to this signal, the output circuit 6 drives the solenoid 7a and the motor 7b of the massaging unit 7 so as to realize the operation designated by the user.

The CPU 3a also drives the display circuit 5 in order to indicate to the user the necessary information such as the contents designated by the user.

The limit switch input circuit 4 is a circuit for defining the range of up/down movement of the massaging unit 7 on the backrest. When the massaging unit 7 goes up or down to the limit, a limit switch is activated to discontinue the up/down movement of the massaging unit 7.

The overall operation of the massaging machine of FIG. 1 based on the biosignal sensed by the biosignal sensing device 2 of the present invention will be described later.

FIRST EMBODIMENT OF BIOSIGNAL SENSING DEVICE

Figure 2:
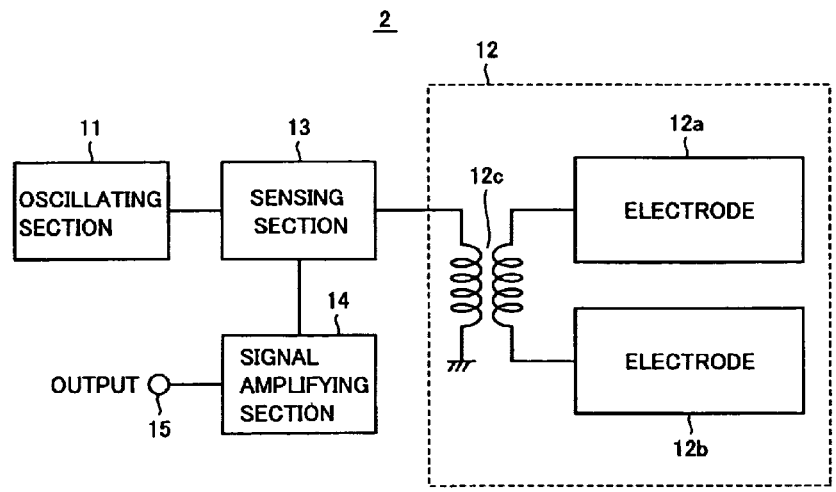
FIG. 2 is a block diagram showing a first embodiment of the biosignal sensing device 2 that is applied to the massaging machine of FIG. 1.

FIG. 2 is a block diagram showing the first embodiment of the biosignal sensing device 2 that is applied to the massaging machine of FIG. 1.

Referring to FIG. 2, the biosignal sensing device 2 includes an oscillating section 11, an electrode section 12, a sensing section 13, a signal amplifying section 14, and an output terminal 15. More specifically, the electrode section 12 includes electrodes 12a, 12b and a transformer 12c.

Operation of the biosignal sensing device 2 will now be roughly described. The oscillating section 11 supplies a high frequency signal, and the electrodes 12a, 12b receive the high frequency signal through the transformer 12c for isolation and real-value conversion. More specifically, a primary winding of the transformer 12c has its both ends connected to the sensing section 13 and the ground potential, respectively, and a secondary winding thereof has its both ends connected to the electrodes 12a, 12b, respectively.

Since the impedance in the electrodes 12a, 12b varies according to the movement of the human body as described below, the high frequency signal energy consumed in the electrodes also varies according to the movement of the human body. Accordingly, variation in the high frequency signal energy that was not consumed in the electrodes is sensed by the sensing section 13 as variation in reflected-wave level. The variation in reflected-wave level thus sensed is amplified and processed in the signal amplifying section 14, and then output from the output terminal 15 as a biosignal. The biosignal thus output is applied to the CPU 3a in FIG. 1.

Figure 3:
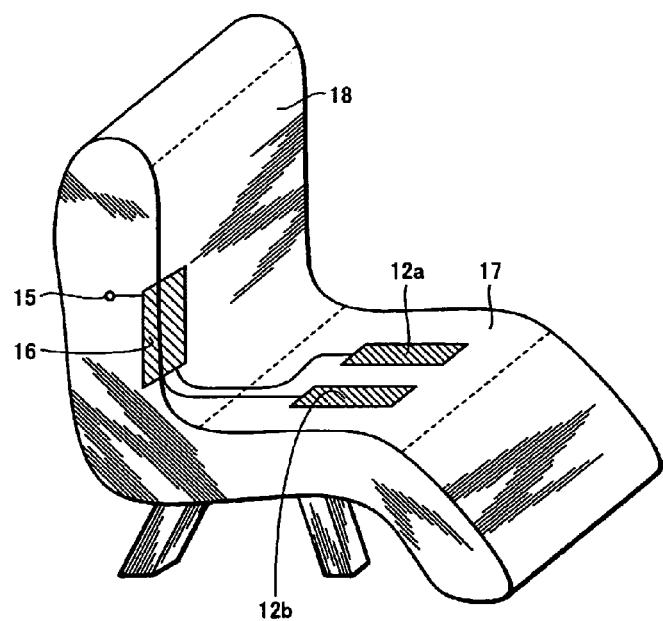
FIG. 3 schematically shows the signal sensing device 2 of FIG. 2 mounted in a chair-type massaging machine.

FIG. 3 schematically shows the signal sensing device 2 of FIG. 2 mounted in a chair-type massaging machine.

Referring to FIG. 3, the electrodes 12a, 12b are arranged on the backside of a surface member of a seat surface 17 in the massaging machine, and a circuit unit 16 integrating other circuit elements, that is, transformer 12c, oscillating section 11, sensing section 13 and signal amplifying section 14 in FIG. 2, is mounted within a backrest 18. Although not shown in the figure, the biosignal output from the output terminal 15 of the circuit unit 16 is applied to the CPU 3a (see FIG. 1) of the operation control section 3 mounted within the massaging machine.

Note that well-known components usually mounted in the backrest 18 such as massaging unit 7 (see FIG. 1) are not shown in FIG. 3. Other circuit elements 4, 5, 6 and 8 in FIG. 1 are also mounted within the massaging machine, although not shown in FIG. 3.

Note that the electrodes 12a, 12b may be arranged at the backrest 18 instead of the seat surface 17. Although not shown in FIG. 3, the electrodes 12a, 12b may be arranged at an armrest in the case of an armchair-type massaging machine. In summary, the electrodes 12a, 12b may be arranged in any part of the massaging machine as long as they can sense the body movement of the user through the surface member of the massaging machine and/or clothes of the user according to the sensing principles described below.

Figure 4:
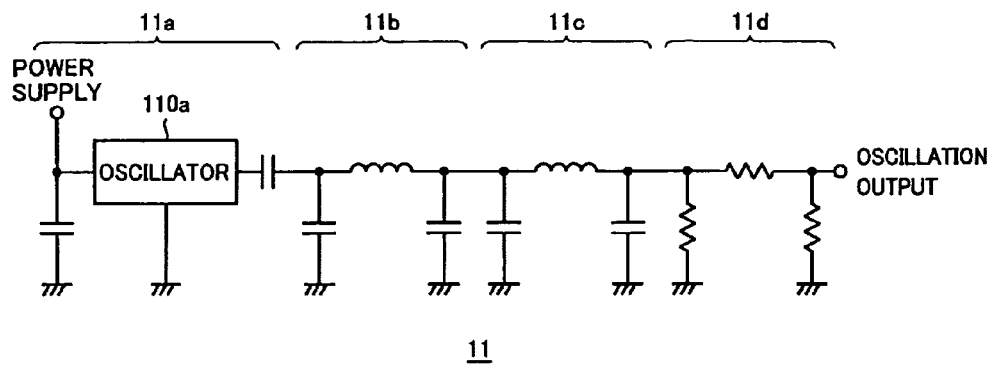
FIG. 4 is a circuit diagram specifically showing the structure of an oscillating section 11 in the biosignal sensing device 2 of the first embodiment of FIG. 2.

FIG. 4 is a circuit diagram specifically showing the structure of the oscillating section 11 in the biosignal sensing device 2 of the first embodiment in FIG. 2.

Referring to FIG. 4, the oscillating section 11 includes an oscillation circuit 11a including an oscillator 110a such as crystal oscillator, for outputting a high-frequency pulse signal, two stages of low pass filters 11b, 11c for converting the pulse signal into sinusoidal signal, and an attenuator 11d.

The reason why the oscillating section 11 outputs a sinusoidal signal as high frequency output is as follows: only in the case of a sinusoidal signal, the energy of sinusoidal components is entirely consumed in the electrodes when the impedance is matched between the oscillating section 11 and the electrodes 11a, 11b, and the reflected-wave level from the electrodes becomes zero. In other words, in the case of a non-sinusoidal signal, the energy of non-sinusoidal components is always reflected from the electrodes serving as a load, regardless of the impedance matching.

Figure 5:
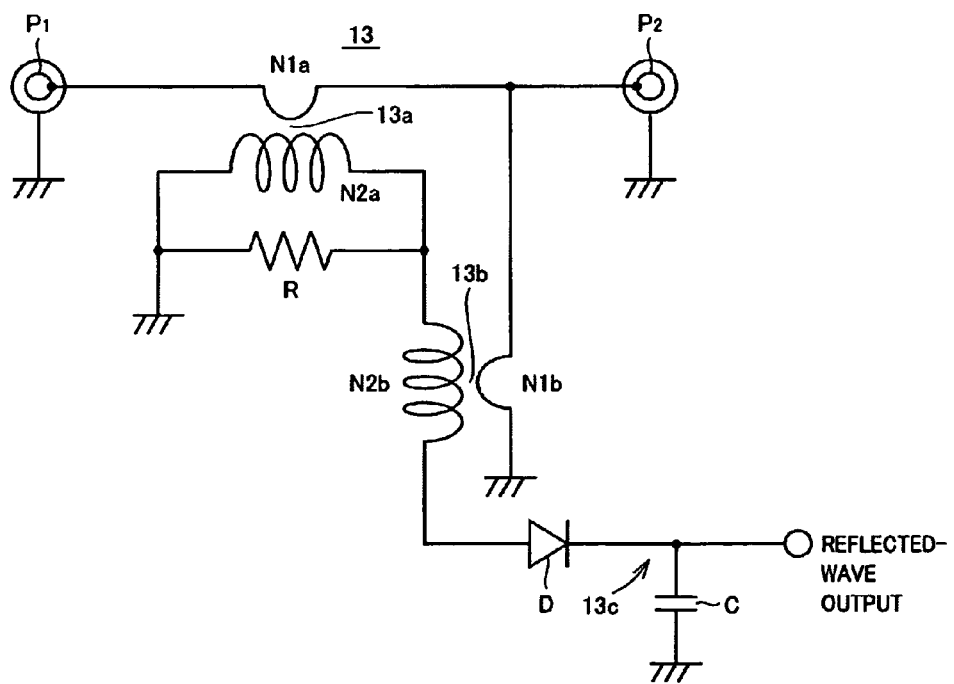
FIG. 5 is a circuit diagram specifically showing the structure of a sensing section 13 in the biosignal sensing device 2 of the first embodiment of FIG. 2.

FIG. 5 is a circuit diagram specifically showing the structure of the sensing section 13 in the biosignal sensing device 2 of the first embodiment in FIG. 2.

The sensing section 13 includes a terminal $P_1$ coupled to the oscillation output of the oscillating section 11, a terminal $P_2$ coupled to the input end of the electrode section 12 (one end of the primary winding of the transformer 12c), M-coupling circuits 13a, 13b having a well-known structure, and a detection circuit 13c.

The M-coupling circuit 13a includes a primary winding N1a inserted between the terminals $P_1$, $P_2$, a secondary winding N2a, and a resistor R connected in parallel to both ends of the secondary winding N2a. The M-coupling circuit 13b includes a primary winding N1b inserted between the terminal $P_2$ and the ground potential, and a secondary winding N2b. Note that the secondary windings N2a, N2b are connected in series between the ground potential and the output end of the sensing section 13. The detection circuit 13c including a diode D and a capacitor C is inserted between one end of the secondary winding N2b and the output end.

Hereinafter, the biosignal detection principles of the sensing section 13 will be described in detail.

For example, it is now assumed that the user is seated on the seat surface 17 properly, i.e., seated so that the buttocks of the user are located on the electrodes 12a, 12b, in the chair-type massaging machine.

When a high-frequency sinusoidal signal from the oscillating section 11 is supplied to the electrodes, a high frequency current flows between the two electrodes 12a and 12b through the surface member of the massaging machine, clothes of the user, and human tissue (mainly, fat) of the user.

A change in distance between the electrode surface and the human body surface due to the body movement corresponds to a change in imaginary component of the high frequency impedance in the electrode. Deformation of the human tissue due to the body movement corresponds to a change in real component of the high-frequency impedance.

Slight body movement of the seated user resulting from pulsation and respiration periodically produces the change in distance and the tissue deformation. As a result, the high impedance in the electrodes changes according to the pulsation and respiration.

Provided that the impedance is matched between the electrodes 12a, 12b, the high frequency signal supplied from the oscillating section 11 is entirely consumed in the electrodes. However, such a change in impedance in the electrodes would vary energy consumption of the electrodes, and the remaining energy would go back as a reflected wave from the electrode section 12 to the oscillating section 11 through the sensing section 13. The M-coupling circuits 13a, 13b of the sensing section 13 form a directional coupler for extracting a part of the energy that was not consumed in the electrodes and applying the extracted energy to the signal amplifying section 14 of the subsequent stage as reflected-wave output.

Note that, the M-coupling circuit using a coil is merely shown as a well-known example of the directional coupler. The sensing section 13 may alternatively be formed from a capacitor, a micro-strip line, and the like.

Figure 6:
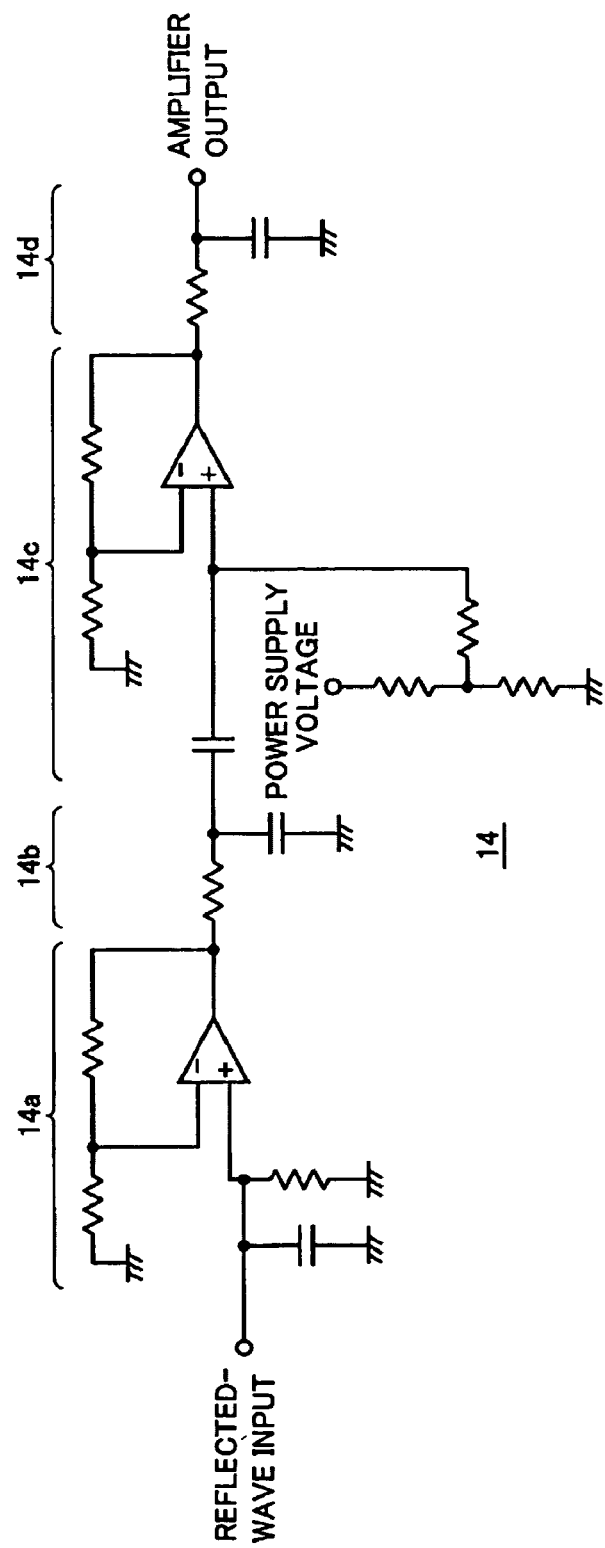
FIG. 6 is a circuit diagram specifically showing the structure of the former stage of a signal amplifying section 14 in the biosignal sensing device 2 of the first embodiment of FIG. 2.

FIG. 6 is a circuit diagram specifically showing the structure of the former stage of the signal amplifying section 14 in the biosignal sensing device 2 of the first embodiment in FIG. 2.

The former stage of the signal amplifying section 14 includes an amplifier 14a, a filter 14b, an amplifier 14c and a filter 14d. As described above, a signal indicating a change in reflected-wave level in the electrodes 12a, 12b is applied from the sensing section 13 to the former stage of the signal amplifying section 14. This signal is then amplified therein and passed through a plurality of filters each having a preset constant, whereby a signal corresponding to pulsation and respiration is extracted.

Figure 7:
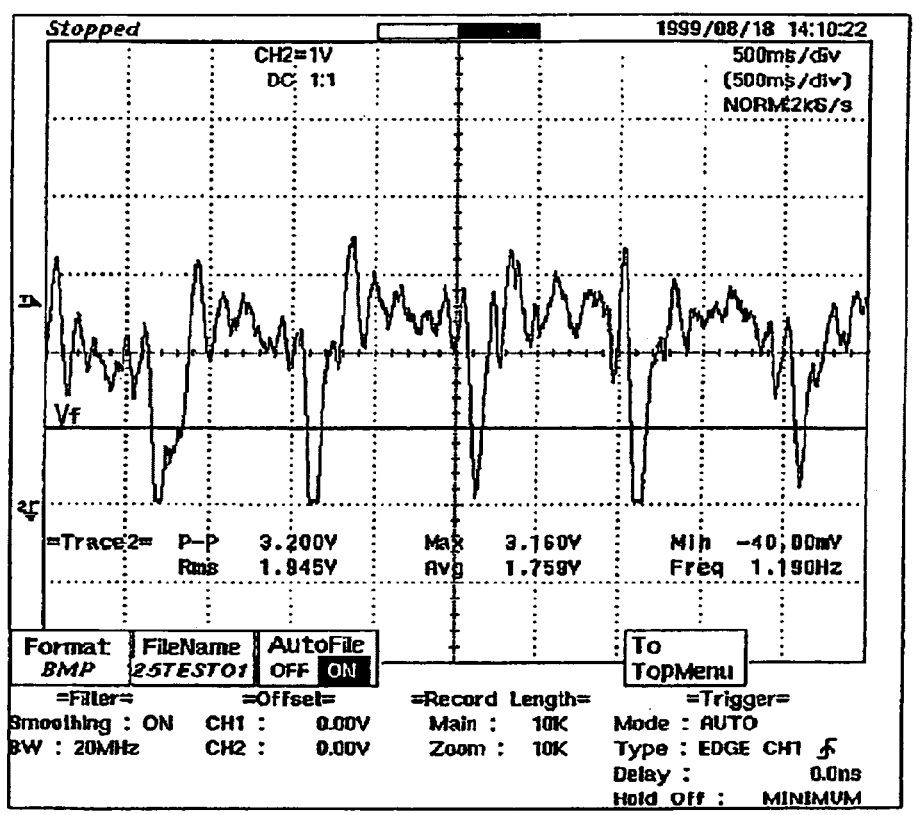
FIG. 7 is a waveform chart showing an actual pulsation waveform obtained by the signal amplifying section 14.

FIG. 7 is a waveform chart showing an actual pulsation waveform obtained by appropriately setting the filter constants of the signal amplifying section 14. The example of FIG. 7 shows a pulsation waveform measured at rest with breath holding.

Such a pulsation waveform is applied to the circuitry in the latter stage of the signal amplifying section 14, in which the pulse-counting operation is counted.

Figure 8A:
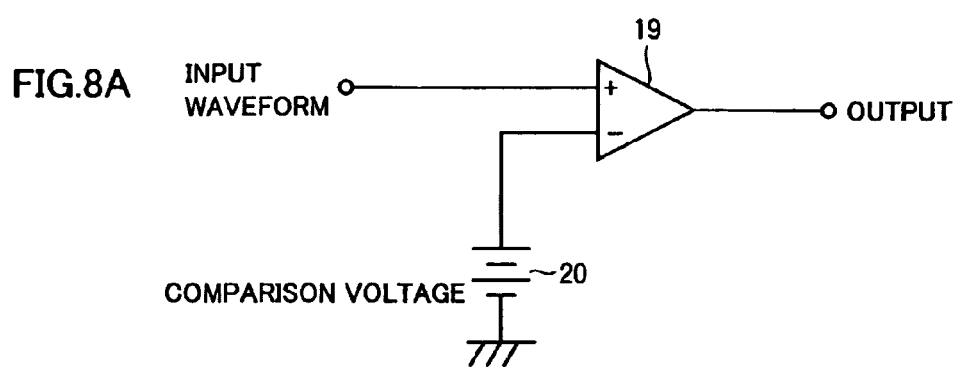
FIG. 8A is a circuit diagram showing the structure of the latter stage of the signal amplifying section 14.
Figure 8B:
FIG. 8B is a waveform chart showing a pulse waveform for counting the pulse rate.

FIG. 8A is a circuit diagram showing the structure of the latter stage of the signal amplifying section 14 for pulse-counting operation. A comparator 19 compares an input signal indicating the pulsation waveform with a fixed comparison voltage supplied from a comparison power supply 20, and outputs a pulse waveform of FIG. 8B. A not-shown counter calculates the pulse rate as a biosignal by counting the number of pulses in the pulse waveform for a fixed period.

Figure 9:
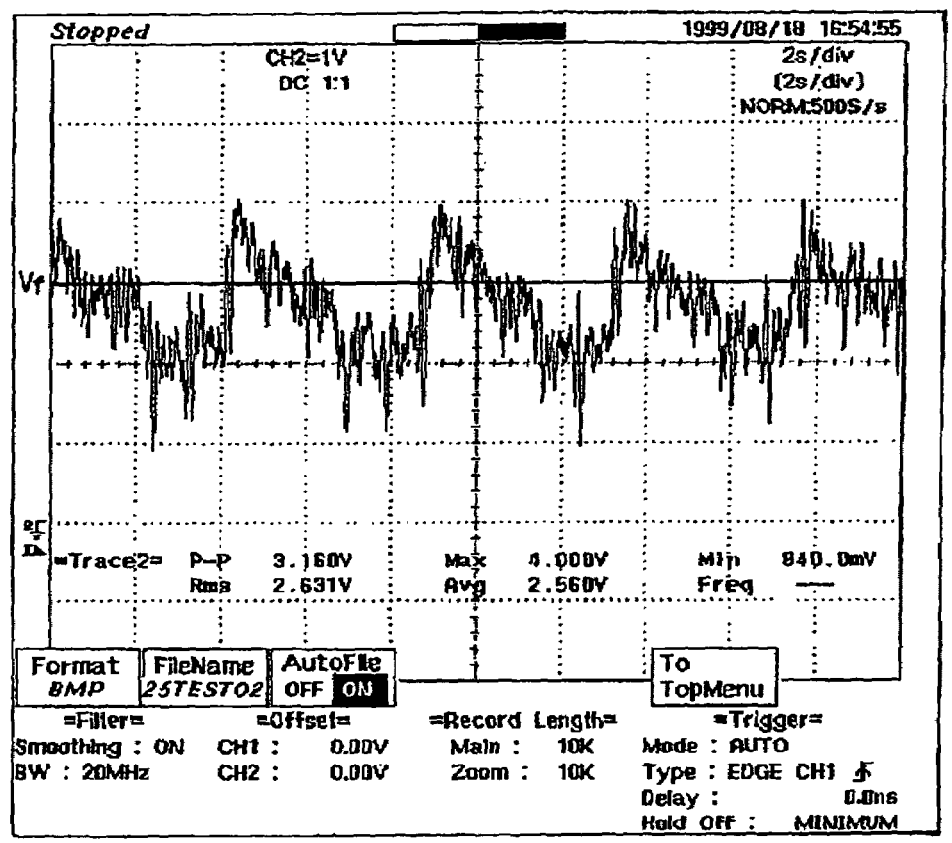
FIG. 9 is a waveform chart showing an actual respiration waveform obtained by the signal amplifying section 14.

FIG. 9 is a waveform chart showing an actual respiration waveform obtained by appropriately setting the filter constants of the signal amplifying section 14 (a fine pulsation waveform is superimposed thereon). The example of FIG. 9 shows a respiration waveform measured at rest with breathing.

Such a respiration waveform is applied to the circuitry in the latter stage of the signal amplifying section 14, in which the respiration-counting operation is conducted.

Figure 10A:
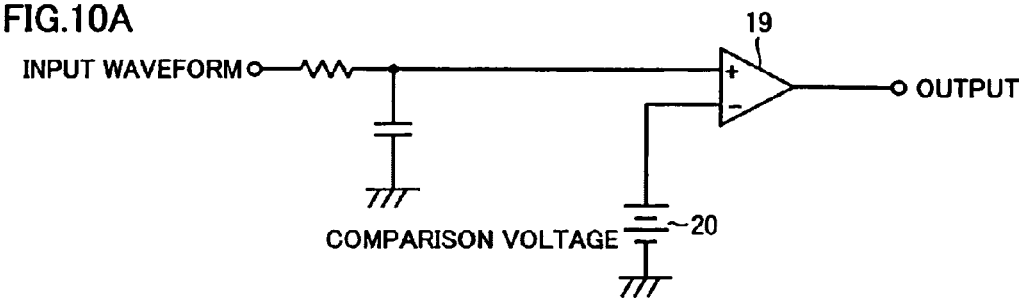
FIG. 10A is a circuit diagram showing the structure of the latter stage of the signal amplifying section 14.

FIG. 10A is a circuit diagram showing the structure of the latter stage of the signal amplifying section 14 for respiration-counting operation. A low pass filter provided in the stage before a comparator 19 filters out the pulsation waveform component from an input biosignal indicating the respiration waveform. The comparator 19 then compares the resultant signal with a fixed comparison voltage supplied from a comparison power supply 20, and outputs the pulse waveform of FIG. 10B. A not-shown counter calculates the respiration rate as a biosignal by counting the number of pulses in the pulse waveform for a fixed period.

Figure 10B:
FIG. 10B is a waveform chart showing a pulse waveform for counting the respiration rate.

Note that the processing in FIGS. 8A and 10B may either be conducted in the signal amplifying section 14 as described above, or in the CPU 3a. Alternatively, the circuitry of FIGS. 8A and 10A may be provided between the signal amplifying section 14 and the CPU 3a in FIG. 6 as external circuitry.

Figure 11:
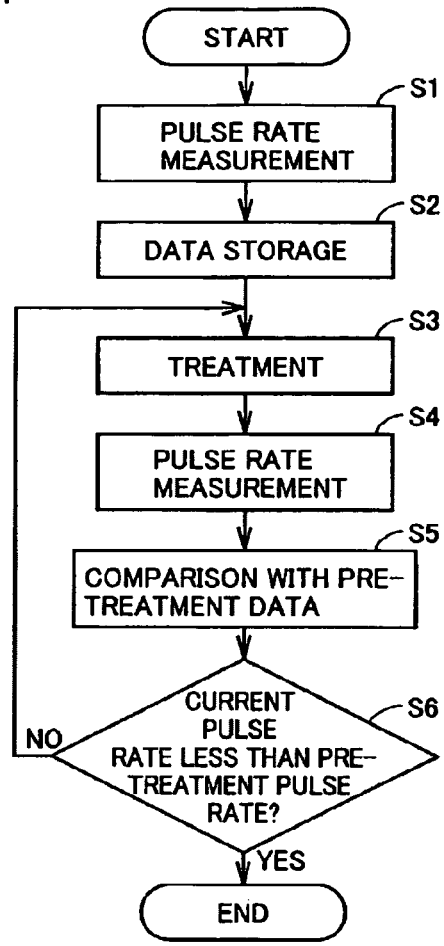
FIG. 11 is a flowchart illustrating massaging operation (treatment method) of a massaging machine according to the present invention.

FIG. 11 is a flowchart illustrating massaging operation (treatment method) conducted by the massaging machine of the present invention by using the biosignal thus obtained from the biosignal sensing device 2 such as pulse rate. Note that such massaging operation is conducted by the CPU 3a based on a program stored in the ROM 3b of the operation control section 3.

First, in response to an instruction to start massaging from the user, the biosignal sensing device 2 measures the pulse rate as described above (Step S1). The pulse rate thus measured is applied to the CPU 3a and stored in the RAM 3b (Step S2).

The pulse rate is continuously measured in Step S4 while giving treatment in Step S3. In Step S5, the pre-treatment pulse rate measured in Step 1 is compared with a current pulse rate measured in Step S4, and whether the current pulse rate is less than the pre-treatment pulse rate or not is determined in Step S6. If it is determined that the current pulse rate is not less than the pre-treatment pulse rate, the routine returns to Step S3 to continue treatment. If it is determined that the current pulse rate is less than the pre-treatment pulse rate, it is determined that the pulse rate is reduced and the user's body is relaxed, and the treatment is automatically terminated.

SECOND EMBODIMENT OF BIOSIGNAL SENSING DEVICE

Figure 12:
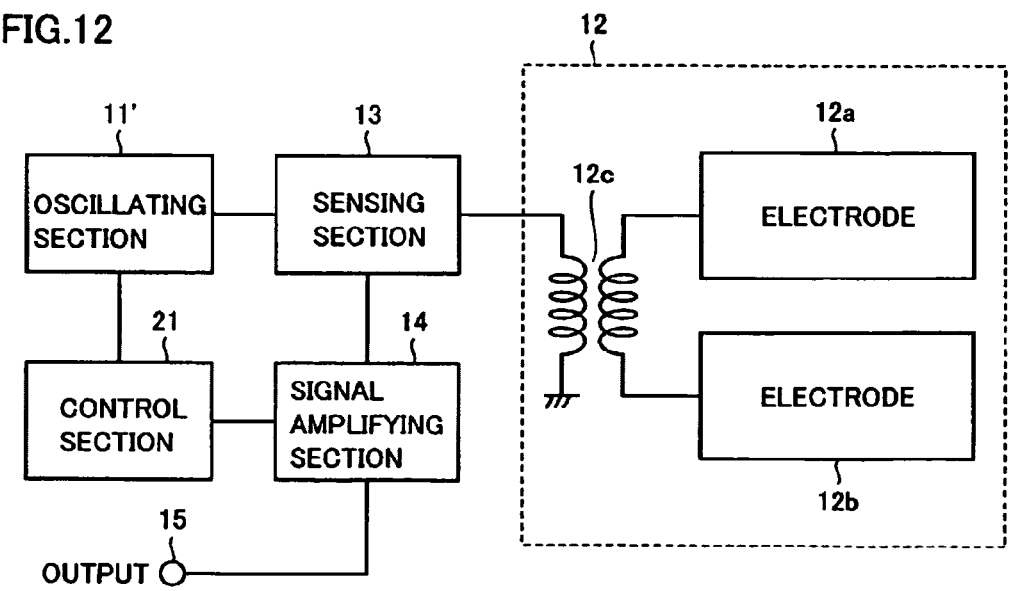
FIG. 12 is a block diagram showing a second embodiment of the biosignal sensing device 2 that is applied to the massaging machine of FIG. 1.

FIG. 12 is a block diagram showing the second embodiment of the biosignal sensing device 2 that is applied to the massaging machine of FIG. 1.

The biosignal sensing device 2 of the second embodiment in FIG. 12 is different from that of the first embodiment in FIG. 2 in the following points, and description of the common parts will not be repeated.

An oscillating section 11' in the biosignal sensing device 2 of FIG. 12 is capable of supplying an oscillation output of a variable oscillation frequency. The biosignal sensing device 2 of FIG. 12 additionally includes a control section 21 for controlling the oscillation frequency of the oscillating section 11' in response to a signal from the signal amplifying section 14.

The biosignal sensing device 2 of the second embodiment monitors the reflected wave from the electrode section 12 while scanning the variable frequency of the oscillating section 11', in order to find an optimal oscillation frequency based on the result.

Figure 13:
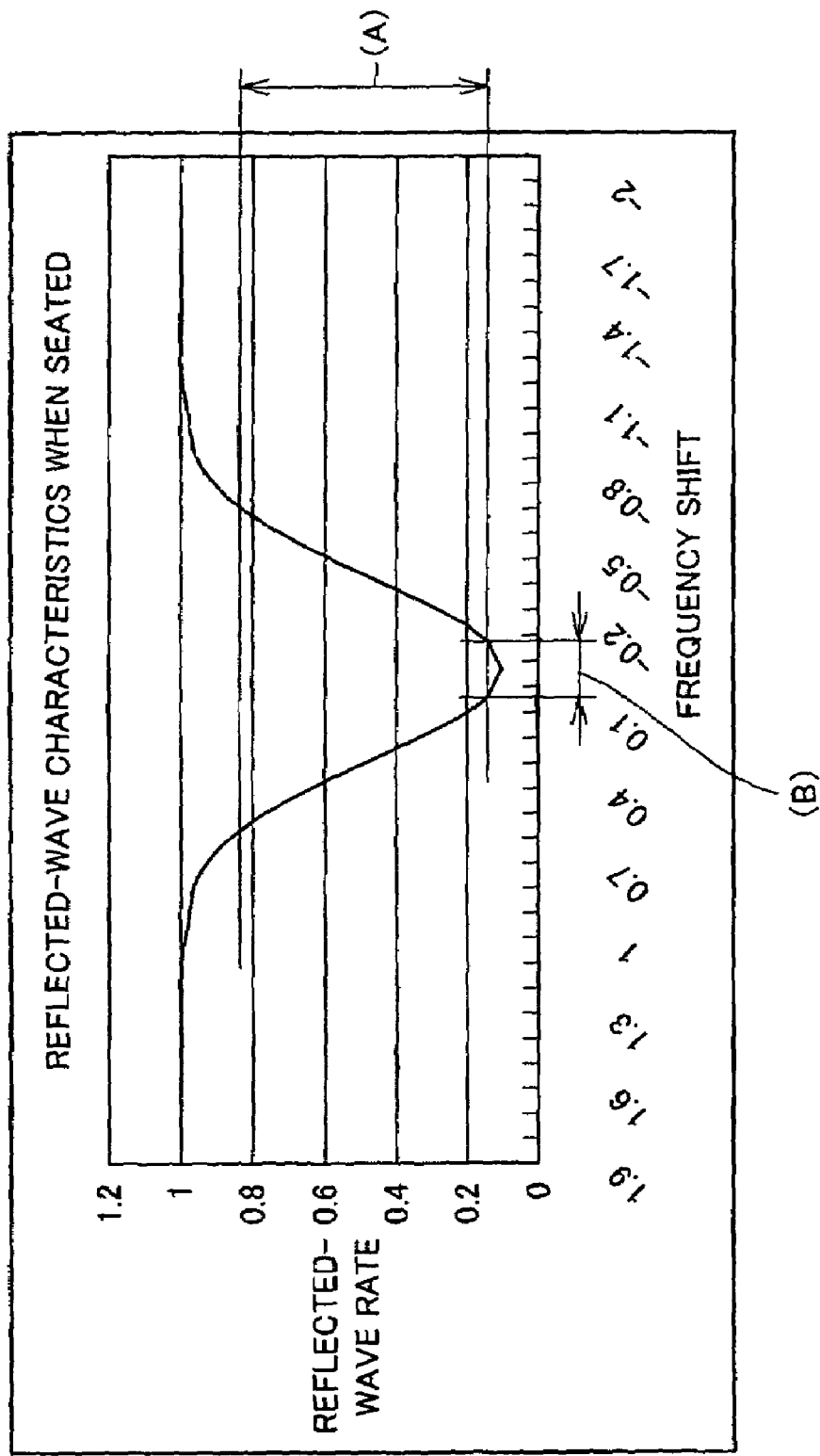
FIG. 13 is a graph showing the reflected-wave characteristics in the case where the user is seated on electrodes.

FIG. 13 is a graph showing the relation between the frequency shift of a high frequency signal in the case where the user is seated on the electrodes 12a, 12b and the corresponding rate of reflected-wave energy from the electrode section 12 (reflected-wave rate). In other words, FIG. 13 is a graph showing the reflected-wave characteristics when the user is seated.

As described before, a change in high frequency impedance in the electrode section 12 includes a change in real component and a change in imaginary component. The change in real component occurs mainly because a real value of the current flowing through the human body changes due to deformation of the human tissue (mainly adipose tissue) caused by the body movement of the seated user. The change in imaginary component occurs mainly because a high frequency component of the current changes due to variation in distance (capacitance) between the electrode surface and the human body surface caused by the body movement. The change in imaginary component contributes much more to the level of impedance change than the change in real component.

Referring back to the graph of the reflected-wave characteristics in FIG. 13, the range shown by arrow (A) is a range where the reflected-wave level changes with a steep gradient with respect to the frequency shift of the high frequency signal due to the change in real component and imaginary component. The detection sensitivity is excellent in this region.

The use of a frequency in the high-sensitivity range (A) enables excellent detection of respiration. However, detection of pulsation is difficult at a frequency in the range (A) because of a great influence of respiration.

More specifically, the body movement resulting from respiration significantly varies the distance between the electrode and the human body, causing an excessive change in imaginary component. Therefore, in the range (A) affected by the change in imaginary component, a change in reflected-wave level resulting from respiration is much greater than that resulting from pulsation, making it impossible to sense pulsation in the same range.

In contrast, the range shown by arrow (B) is a range of the minimum reflected-wave characteristics. This range is approximately flat when magnified. In other words, in the flat range (B), the reflected-wave level does not change with respect to a change in frequency (change in imaginary component), but changes with respect to a change in real component alone.

Although a change in frequency (change in imaginary component) dominates the change in reflected-wave level resulting from respiration, not only a change in imaginary component but also a change in real component dominate the change in reflected-wave level resulting from pulsation.

Accordingly, the use of a high frequency signal in the range (B) of the minimum reflected-wave characteristics enables detection of a reflected-wave level resulting only from the real component, making it possible to sense the pulsation alone without being affected by respiration.

As has been described above, in order to sense respiration, it is preferable to use an oscillation frequency in the steep-gradient region of the range (A). In order to sense pulsation, it is preferable to use an oscillation frequency in the minimum-value region of the range (B). For example, the oscillation frequency in the oscillating section 11 of the first embodiment in FIG. 2 may be fixed to a frequency in the range (A) or (B) according to the detection purpose (respiration or pulsation), based on the graph of reflected-wave characteristics that is experimentally obtained in advance as shown in FIG. 13.

In contrast, in the second embodiment of FIG. 12, the reflected-wave level from the electrode section 12 is first monitored in the control section 21 through the signal amplifying section 14 while scanning a variable oscillation frequency of the oscillating section 11'. The reflected-wave characteristics of FIG. 13 are thus obtained. An oscillation frequency corresponding to the detection purpose is then selected based on the reflected-wave characteristics.

Figure 14:
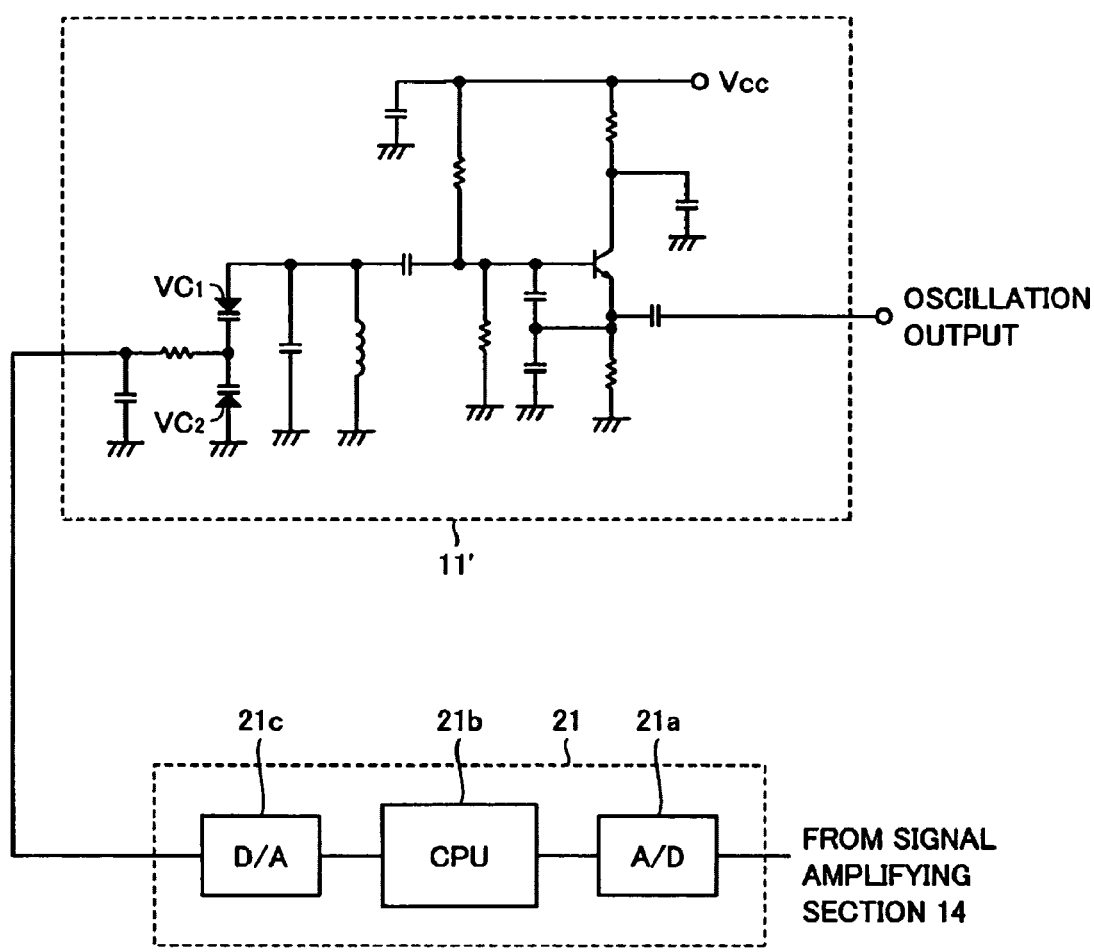
FIG. 14 is a circuit diagram specifically showing the structure of an oscillating section 11' and a control section 21 of FIG. 12.

FIG. 14 is a circuit diagram specifically showing the structure of the oscillating section 11' and the control section 21 of FIG. 12.

In FIG. 14, a CPU 21b in the control section 21 generates a control signal for varying the oscillation frequency of the oscillating section 11'. A D-A converter 21c converts this control signal into an analog direct current (DC) voltage for output to variable capacitors $VC_1$, $VC_2$ of the oscillating section 11'. When the analog DC voltage is changed within a prescribed range, the capacitance of the variable capacitors $VC_1$, $VC_2$ and thus the oscillation frequency of the oscillating section 11' also change accordingly. As a result, the high-frequency impedance in the electrode section 12 and thus the reflected-wave level from the electrode section 12 also change accordingly.

A reflected-wave level signal from the electrode section 12 is applied to the control section 21 from the sensing section 13 through the signal amplifying section 14. The reflected-wave level signal is converted into digital signal by an A-D converter 21a of the control section 21, and then applied to the CPU 21b. By such a single frequency scan, the CPU 21b obtains the reflected-wave characteristics data as shown in FIG. 13. The CPU 21b then sets the oscillation frequency of the oscillating section 11' to an appropriate value in the range (A) or (B) according to the detection purpose, i.e., respiration or pulsation.

The high frequency impedance in the electrode section 12 and the oscillation frequency matched therewith also change due to the factors such as characteristics of the body tissue and sitting posture of the seated user. In the biosignal sensing device 2 of the first embodiment in FIG. 2, the frequency of the high frequency signal supplied from the oscillating section 11 is fixed in advance regardless of the user. In contrast, in the second embodiment of FIG. 12, the oscillation frequency is scanned while the user is seated before treatment, and an optimal oscillation frequency is found based on the reflected-wave characteristics data suitable for the user (characteristics of the body tissue and sitting posture of the user). Therefore, a biosignal can always be sensed by using the optimal oscillation frequency for the detection purpose (respiration or pulsation).

Note that, in the case where the oscillating section 11 has a fixed oscillation frequency as in the first embodiment of FIG. 2, an optimal oscillation frequency can not always be used. This is because the reflected-wave characteristics vary depending on the characteristics of the body tissue and sitting posture of the user actually seated in the massaging machine.

Figure 15:
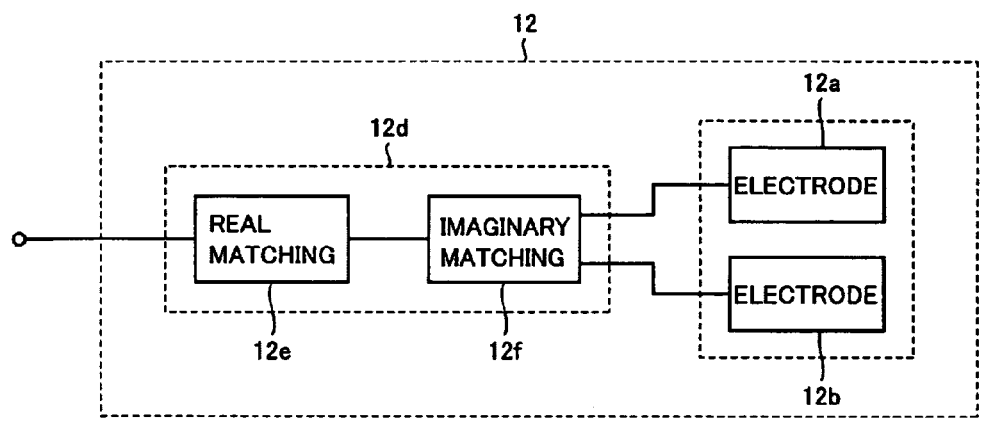
FIG. 15 is a functional block diagram showing an electrode section 12 having an automatic impedance matching function.

In view of this, in a modification of the electrode section 12 in FIG. 15, the electrode section 12 automatically matches the real component and imaginary component of the high frequency impedance in the case where the oscillating section 11 has a fixed oscillation frequency. A high frequency impedance state suitable for respiration detection or a high frequency impedance state suitable for pulsation detection is thus realized on the reflected-wave characteristics as shown in FIG. 13.

FIG. 15 is a functional block diagram of such an electrode section 12. Referring to FIG. 15, the electrode section 12 includes an automatic impedance matching section 12d in the stage before the electrodes 12a, 12b. The automatic impedance matching section 12d includes a real matching section 12e for automatically matching the real component of the high frequency impedance of the electrode section 12, and an imaginary matching section 12f for automatically matching the imaginary component of the high frequency impedance of the electrode section 12.

Figure 16:
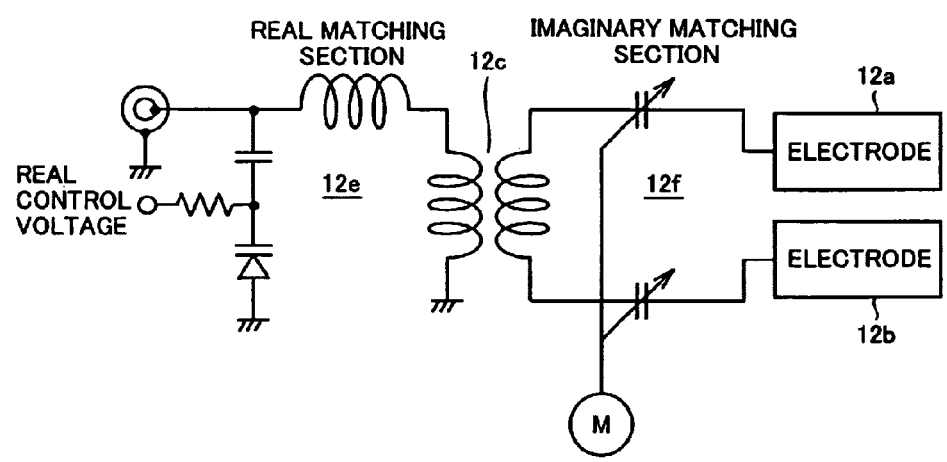
FIG. 16 is a circuit diagram showing an example of a circuit implementing the impedance matching function of FIG. 15.

FIG. 16 is a circuit diagram showing an example of the circuit implementing the automatic impedance matching section 12d in the functional block diagram of FIG. 15. Referring to FIG. 16, a not-shown control section (CPU) applies a real control voltage to the real matching section 12e, and applies to the imaginary matching section 12f a signal for driving a motor M for controlling the capacitance of a variable capacitor.

Figure 17:
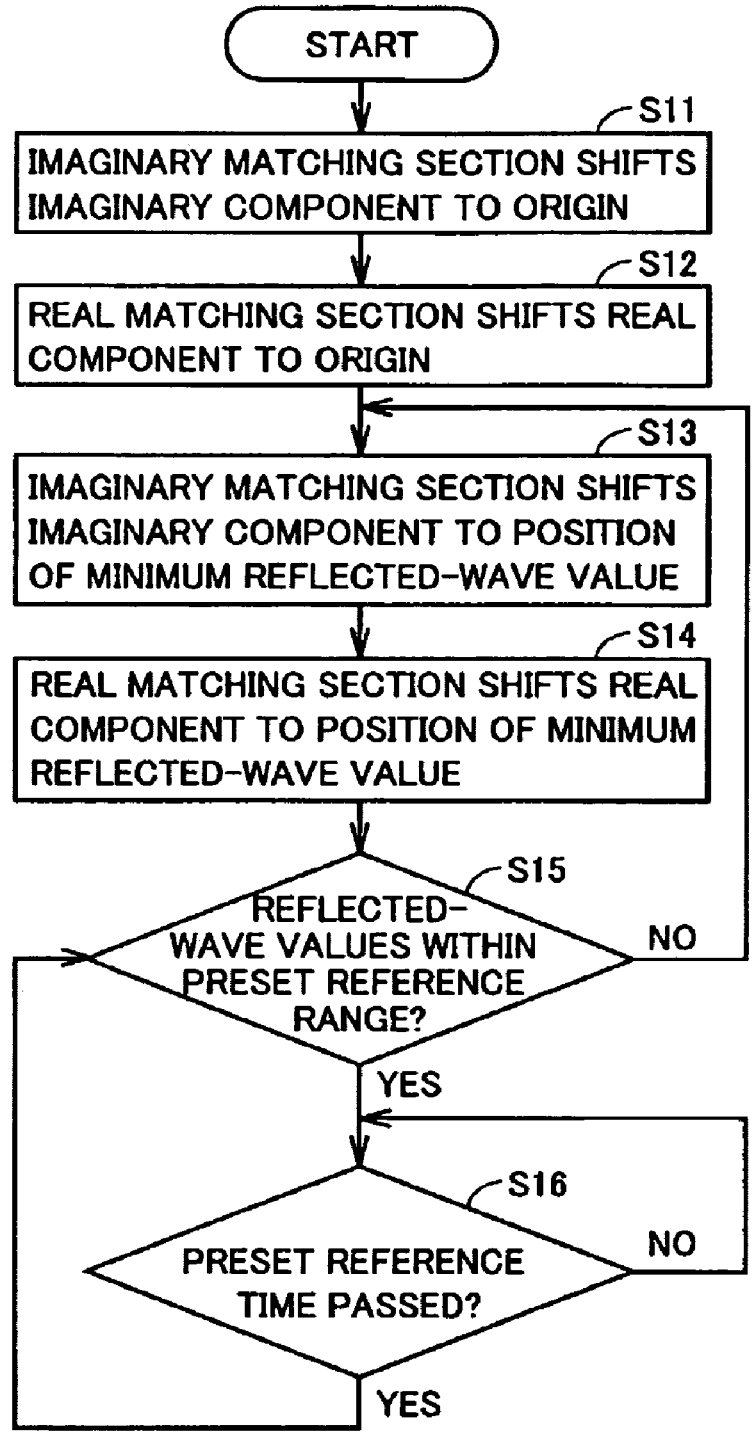
FIG. 17 is a flowchart illustrating automatic impedance matching operation conducted by the electrode section 12 of FIG. 15 for pulsation detection.

FIG. 17 is a flowchart illustrating pulsation detection operation of such an automatic impedance matching section 12d.

Referring to FIG. 17, the imaginary matching section 12f first shifts an imaginary component to the origin (Step S11), and the real matching section 12e shifts a real component to the origin (Step S12).

The imaginary matching section 12f then shifts the imaginary component to the position of the minimum value on the reflected-wave characteristics diagram as shown in FIG. 13 (Step S13), and the real matching section 12e shifts the real component to the position of the minimum value on the reflected-wave characteristics diagram (Step S14).

If it is determined that the respective reflected-wave values at the shifted positions of the imaginary component and the real component are within a preset reference range (Step S15), it is determined that the reflected-wave values have reached the minimum-value region suitable for pulsation detection. If it is determined that the reflected-wave values are not within the preset reference range (Step S15), it is determined that the reflected-wave values have not reached the minimum value, whereby the imaginary component and the real component are continuously shifted in Steps S13 and S14.

If it is determined in Step S15 that the reflected-wave values have reached the minimum-value region, whether preset reference time has passed or not is determined (Step S16). If it is determined that the preset reference time has passed, the routine returns to Step S15 to determine if the reflected-wave values are still in the minimum-value range.

The loop of Steps S15 and S16 is repeated as long as the reflected-wave values are in the minimum-value region. During the repetition, pulsation detection can be continued in an excellent manner without being affected by the imaginary component.

If it is determined in Step S15 in the repetition that the reflected-wave values go out of the minimum-value region, the imaginary component and the real component are further adjusted in Steps S13 and S14. The impedance is thus automatically matched so that pulsation detection can be reliably continued in an excellent manner in the minimum-value region of the reflected-wave values.

Figure 18:
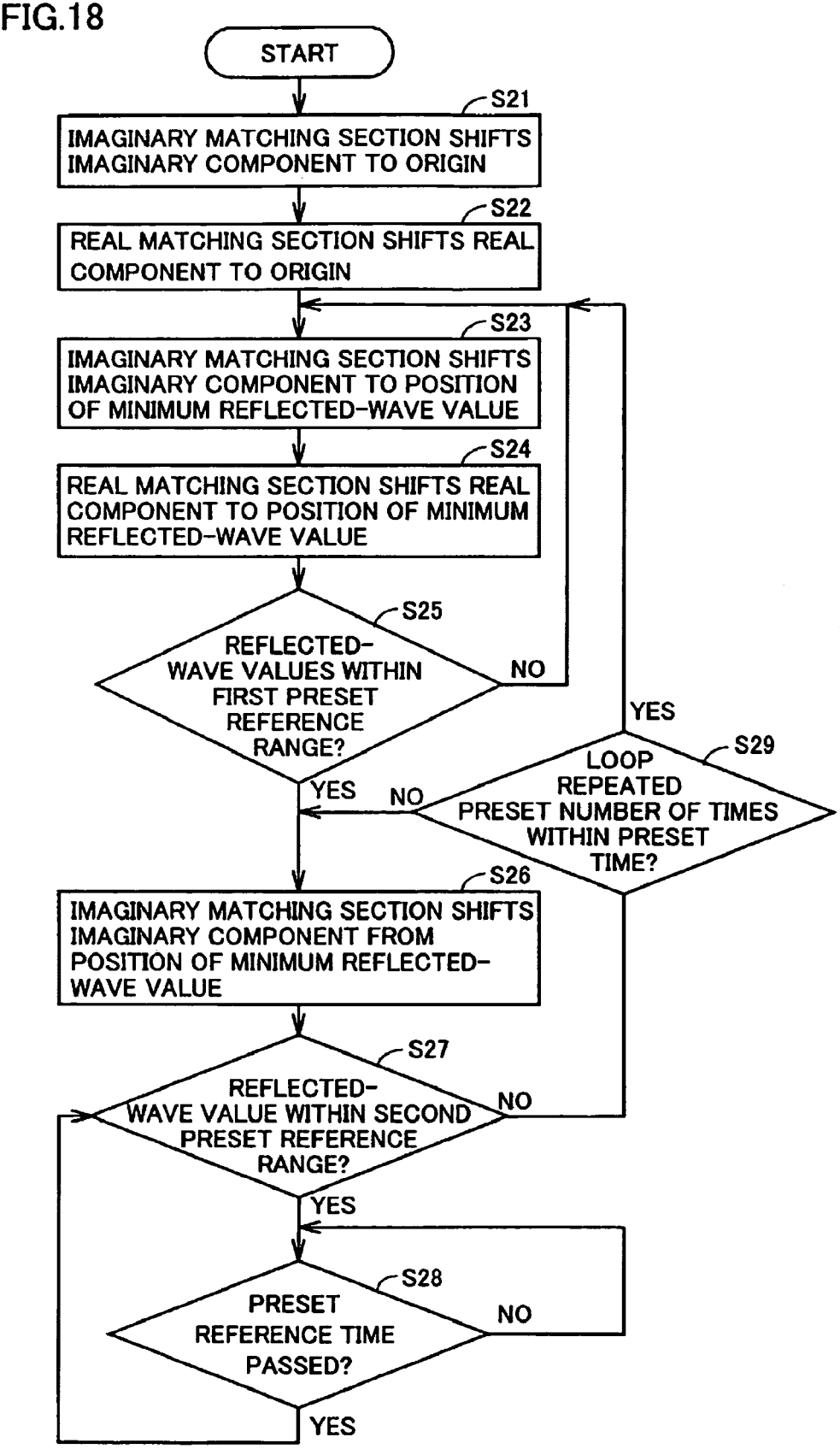
FIG. 18 is a flowchart illustrating automatic impedance matching operation conducted by the electrode section 12 of FIG. 15 for respiration detection.

FIG. 18 is a flowchart illustrating respiration detection operation of the automatic impedance matching section 12d.

Referring to FIG. 18, the imaginary matching section 12f first shifts an imaginary component to the origin (Step S21), and the real matching section 12e shifts a real component to the origin (Step S22).

The imaginary matching section 12f then shifts the imaginary component to the position of the minimum value on the reflected-wave characteristics diagram as shown in FIG. 13 (Step S23), and the real matching section 12e shifts the real component to the position of the minimum value on the reflected-wave characteristics diagram (Step S24).

If it is determined that the respective reflected-wave values at the shifted positions of the imaginary component and the real component are within a first preset reference range (Step S25), it is determined that the reflected-wave values have reached the minimum-value region. If it is determined that the reflected-wave values are not within the preset reference range (Step S25), it is determined that the reflected-wave values have not reached the minimum value, whereby the imaginary component and the real component are continuously shifted in Steps S23 and S24.

If it is determined in Step S25 that the reflected-wave values have reached the minimum-value region that is not affected by the imaginary component, the imaginary matching section 12f shifts the imaginary component in a prescribed direction on the reflected-wave characteristics diagram (Step S26). As a result, the imaginary component enters a steep-gradient region of the reflected-wave characteristics dominated by the imaginary component. If it is determined that the reflected value at the shifted position is within a second preset reference range (Step S27), it is determined that the high-frequency impedance in the electrode is within the range suitable for respiration detection. It is then determined whether preset reference time has passed or not (Step S28). If it is determined that the preset reference time has passed, the routine returns to Step S27 to determine if the reflected-wave value is still in the steep-gradient region.

The loop of Steps S27 and S28 is repeated as long as the reflected-wave value is in the steep-gradient region. During the repetition, detection of respiration dominated by the imaginary component can be continued in an excellent manner.

If it is determined in Step S27 in the repetition that the reflected-wave value goes out of the steep-gradient region, it is determined whether the loop of Steps S27 and S28 is repeated a preset number of times within preset time or not (Step S29).

If the loop is not repeated the preset number of times, the routine returns to Step S26, where the imaginary component is continuously shifted. If the loop is repeated the preset number of times, the routine returns to Steps S23 and S24, where the respective reflected-wave values are returned to the position of the minimum value, and shifting to the steep-gradient region is then conducted again.

Thus, the imaginary component and the real component are further adjusted in Steps S26, S23 and S24. Therefore, the impedance is automatically matched so that respiration detection can be reliably continued in an excellent manner in the steep-gradient region of the reflected-wave value.

THIRD EMBODIMENT OF BIOSIGNAL SENSING DEVICE

Figure 19:
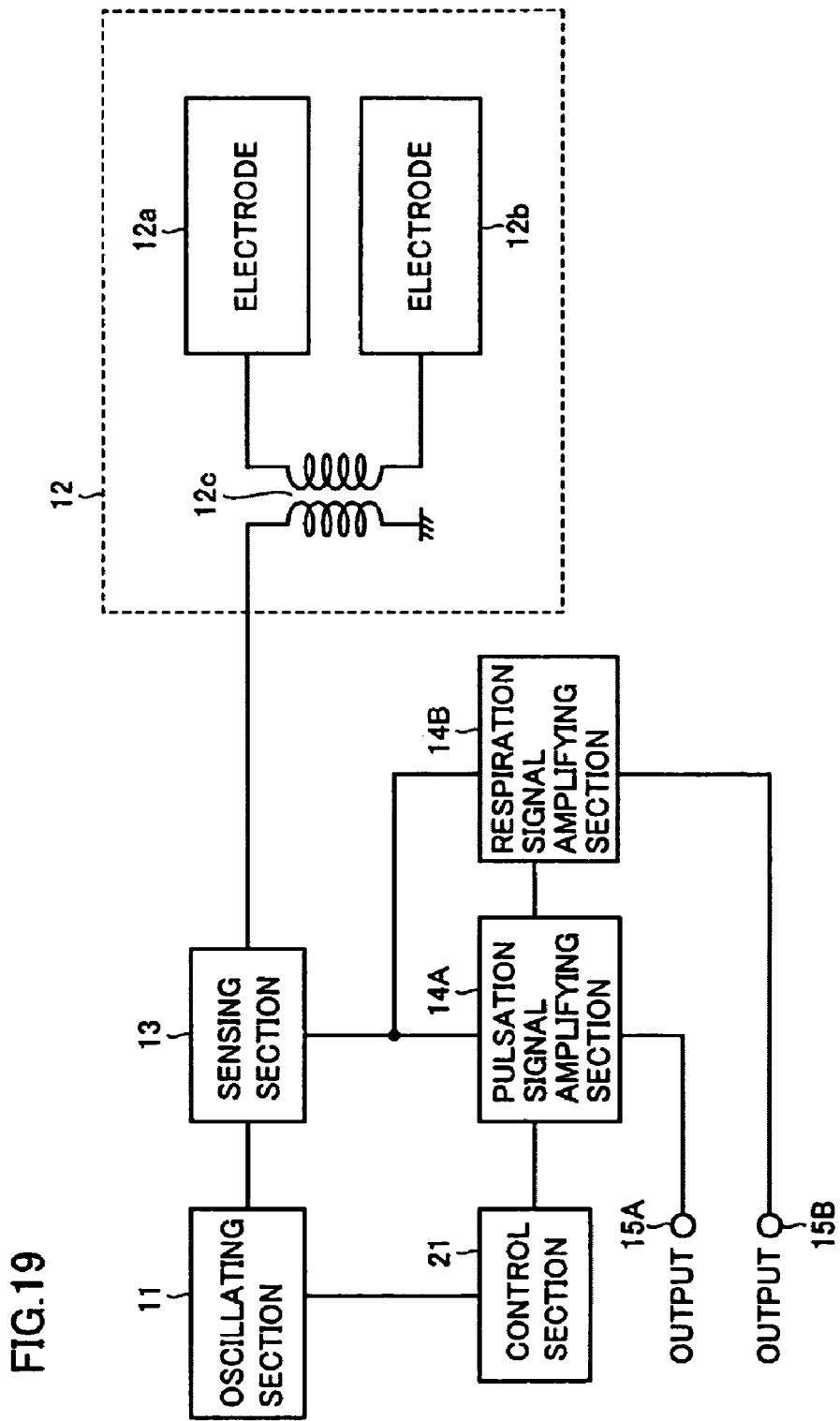
FIG. 19 is a block diagram showing a third embodiment of the biosignal sensing device 2 that is applied to the massaging machine of FIG. 1.

FIG. 19 is a block diagram showing the third embodiment of the biosignal sensing device 2 that is applied to the massaging machine of FIG. 1.

The biosignal sensing device 2 of FIG. 19 is the same as that of the second embodiment in FIG. 12 except for the following point: the signal amplifying section 14 of the embodiment in FIG. 12 is divided into a pulsation signal amplifying section 14A having a preset filter constant for extracting a pulsation waveform and a respiration signal amplifying section 14B having a preset filter constant for extracting a respiration waveform.

As a result, biosignals indicating the pulse rate and the respiration rate can be independently output from output terminals 15A and 15B, respectively.

Note that, in order to obtain the pulse rate, the oscillation frequency of the oscillating section 11' is set to the minimum-value region of the reflected-wave characteristics according to the reflected-wave level signal applied from the sensing section 13 to the control section 21 through the signal amplifying section 14A, as in the second embodiment of FIG. 12.

FOURTH EMBODIMENT OF BIOSIGNAL SENSING DEVICE

Figure 20:
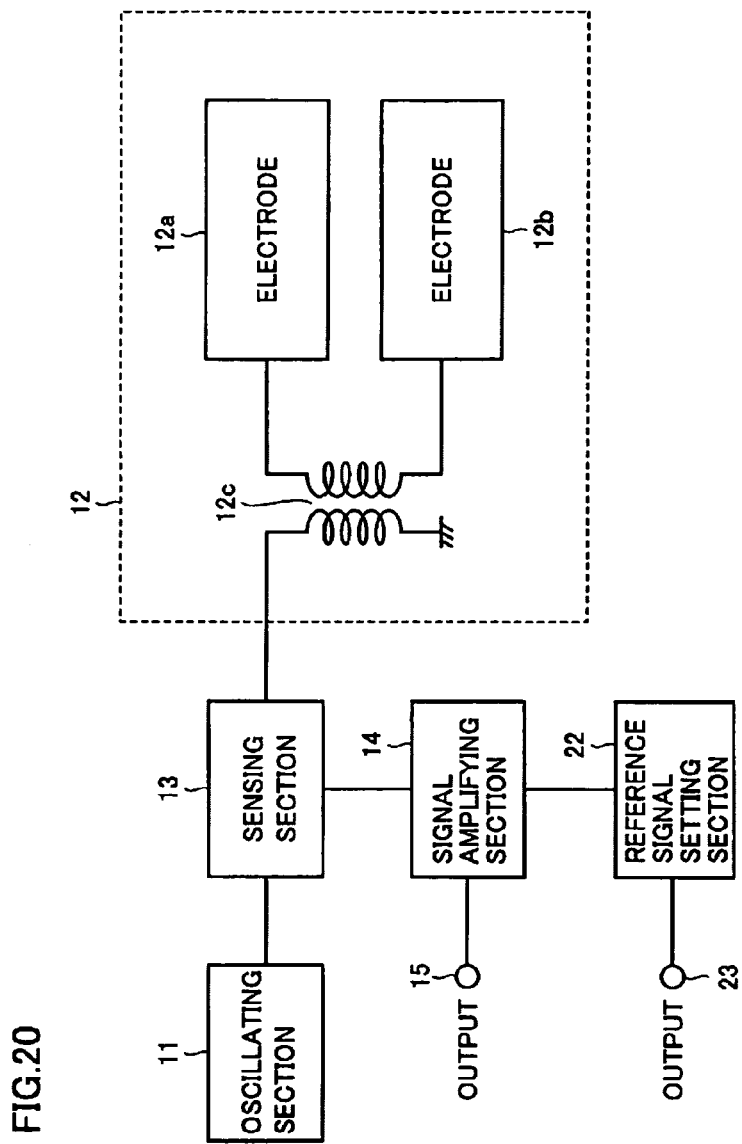
FIG. 20 is a block diagram showing a fourth embodiment of the biosignal sensing device 2 that is applied to the massaging machine of FIG. 1.

FIG. 20 is a block diagram showing the fourth embodiment of the biosignal sensing device 2 that is applied to the massaging machine of FIG. 1. The biosignal sensing device 2 of FIG. 20 is the same as that of the first embodiment in FIG. 2 except for the following point: the biosignal sensing device 2 of this embodiment further includes a reference signal setting section 22 and an output terminal 23 in addition to the structure of FIG. 2.

For example, in the case of a chair-type massaging machine, baggage may be placed on the seat surface instead of the human body, or the user may be seated in an improper posture. In such a case, the user must be notified of the fact that a biosignal cannot be sensed correctly.

When the user is seated properly, the impedance is matched, and the reflected-wave level from the electrodes is reduced. In contrast, when an object other than the human body is placed or the user is not properly seated, the impedance is not matched, and the reflected-wave level from the electrode is increased.

Accordingly, the intermediate level thereof is set as a reference level. In this case, if the reflected-wave level is less than the reference level, it is determined that the user is seated properly. If the reflected-wave level exceeds the reference level, it is determined that an object other than the human body is placed on the seat surface or that the user is seated in an improper posture.

In the embodiment of FIG. 20, the reference signal setting section 22 has such an intermediate level as a preset reference level, so that the above determination is made based on the reflected-wave level obtained from the sensing section 13 through the signal amplifying section 14.

Figure 21:
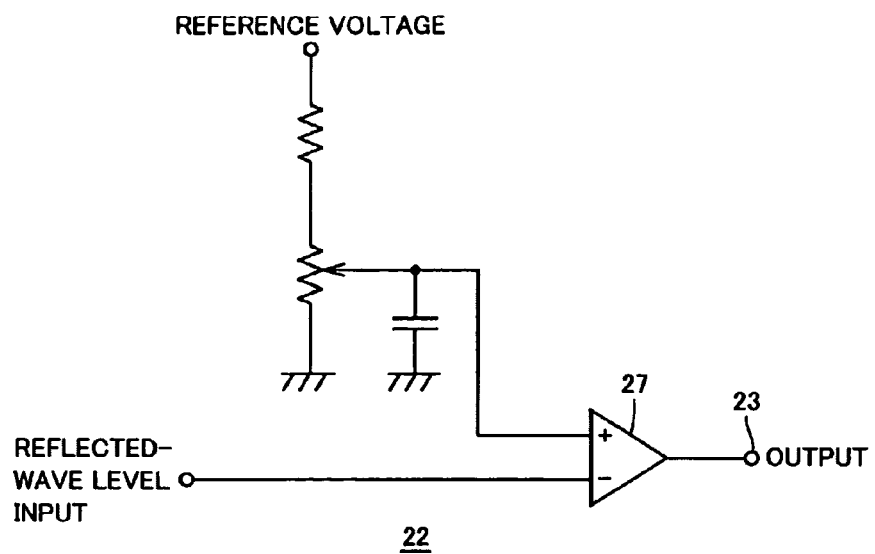
FIG. 21 is a circuit diagram showing the structure of a reference signal setting section 22 of FIG. 20.

FIG. 21 is a circuit diagram showing the structure of the reference signal setting section 22. In FIG. 21, a comparator 27 compares the reflected-wave level received from the sensing section 13 through the signal amplifying section 14 of FIG. 20 with the reference voltage as the intermediate level, and outputs the comparison result from the output terminal 23. This information is applied to the CPU 3a of FIG. 1 for use in necessary control and display.

FIFTH EMBODIMENT OF BIOSIGNAL SENSING DEVICE

Figure 22:
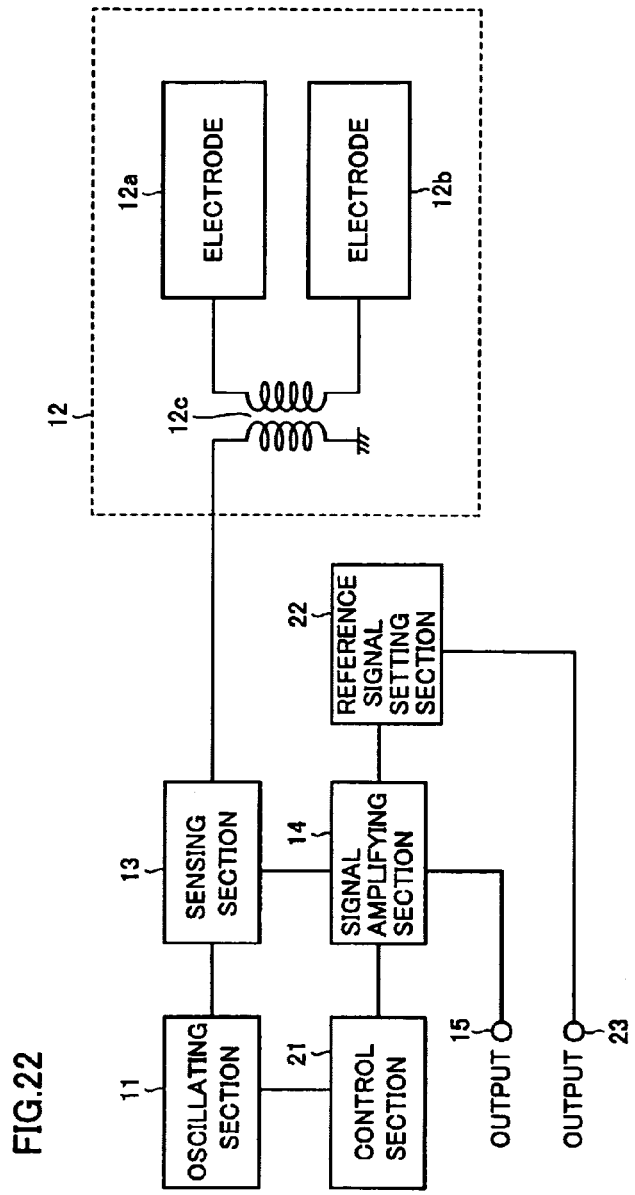
FIG. 22 is a block diagram showing a fifth embodiment of the biosignal sensing device 2 that is applied to the massaging machine of FIG. 1.

FIG. 22 is a block diagram showing the fifth embodiment of the biosignal sensing device 2 that is applied to the massaging machine of FIG. 1.

The embodiment of FIG. 22 corresponds to the second embodiment of FIG. 12 additionally including the reference signal setting section 22 and the output terminal 23 of the fourth embodiment in FIG. 20. Since the structure is otherwise the same as that of the second embodiment in FIG. 12, description thereof will not be repeated.

Note that, in each of the above embodiments, a pair of electrodes having the same shape are used as the electrodes 12a, 12b, and the electrodes 12a, 12b are positioned symmetrically with each other in the horizontal or vertical direction so that a part of the user's body is reliably in contact with or located dose to the electrodes when the user is seated.

For reduced common-mode current and improved sensitivity, each electrode need be shaped symmetrically in the horizontal and vertical directions. The electrodes may have any shape according to the detection purpose as long as the above condition is satisfied.

Figure 23:
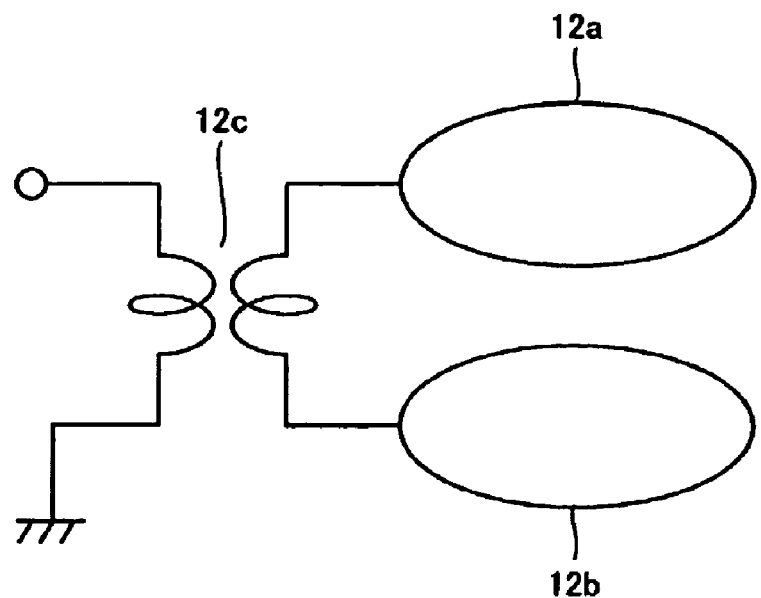
FIG. 23 is a schematic diagram showing another form of electrodes 12a, 12b.
Figure 24:
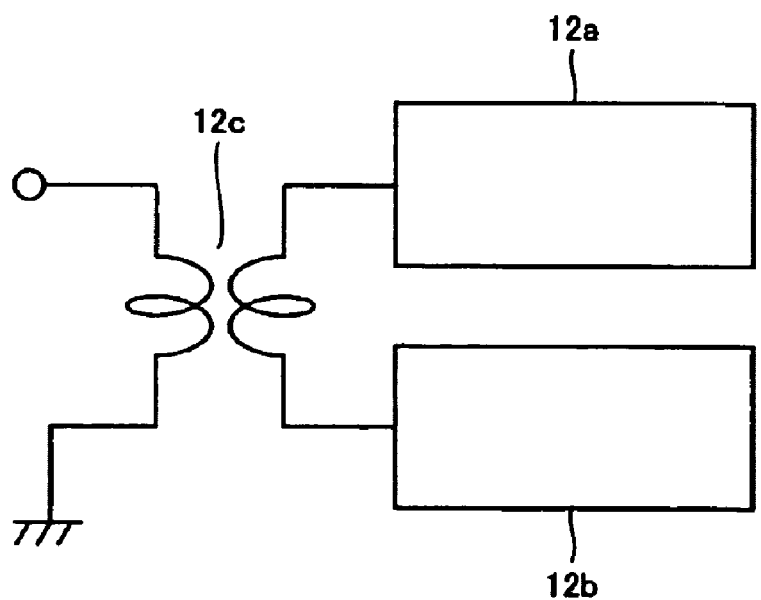
FIG. 24 is a schematic diagram showing still another form of the electrodes 12a, 12b.

For example, FIG. 23 is a schematic diagram of elliptic electrodes 12a, 12b. FIG. 24 is a schematic diagram of rectangular electrodes 12a, 12b.

Figure 25:
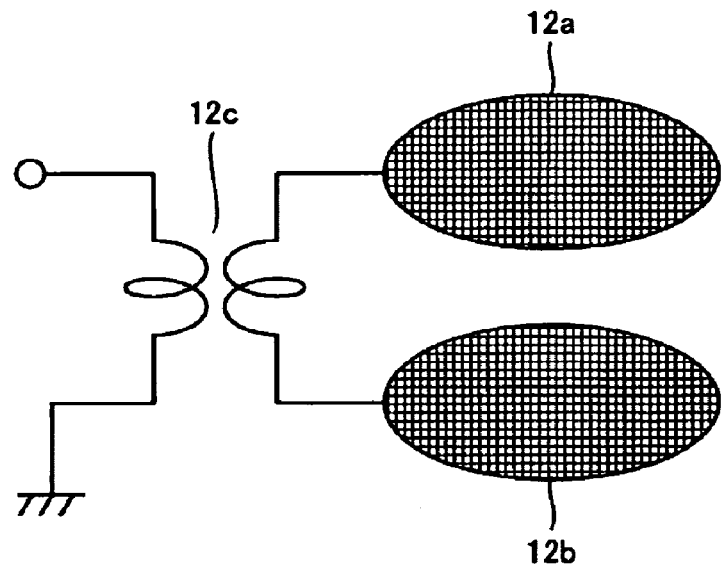
FIG. 25 is a schematic diagram showing yet another form of the electrodes 12a, 12b.

It is desirable to use a flexible electrode, for example, a mesh electrode in order to prevent the user from feeling uncomfortable when seated on, or in contact with, the electrode,. FIG. 25 is a schematic diagram of elliptic mesh electrodes 12a, 12b, and FIG. 26 is a schematic diagram of rectangular mesh electrodes 12a, 12b.

Figure 26:
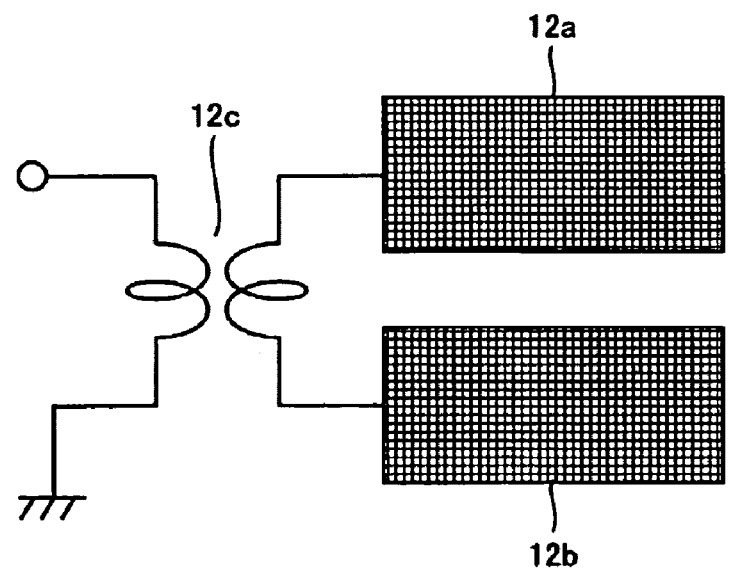
FIG. 26 is a schematic diagram showing a further form of the electrodes 12a, 12b.

The use of the mesh electrodes as shown in FIGS. 25 and 26 ensures flexibility of the electrodes without degrading high-frequency characteristics thereof. Note that the electrodes are preferably formed from a material such as silver, gold, copper or aluminum.

Figure 27:
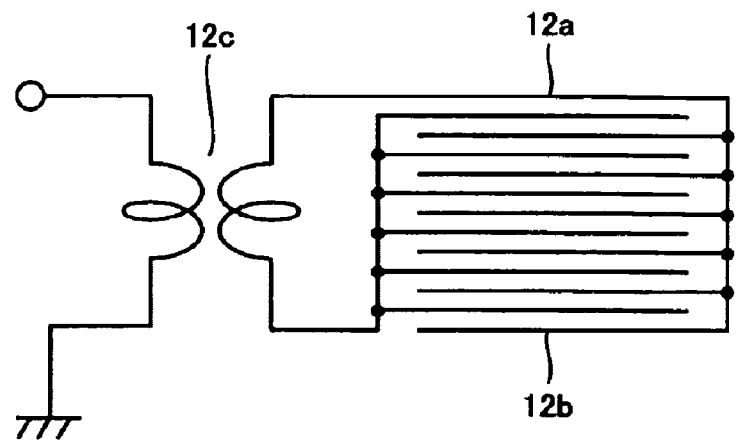
FIG. 27 is a schematic diagram showing a still further form of the electrodes 12a, 12b.
Figure 28:
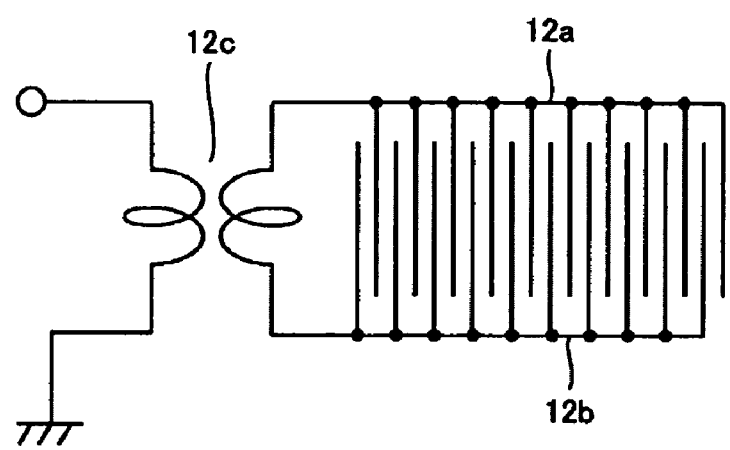
FIG. 28 is a schematic diagram showing a yet further form of the electrodes 12a, 12b.

For flexibility of the electrodes, it is also preferable to use comb-like electrodes. FIG. 27 is a schematic diagram of the electrodes 12a, 12b having their comb teeth arranged in parallel with the longitudinal direction of the electrodes, and FIG. 28 is a schematic diagram of the electrodes 12a, 12b having their comb teeth arranged perpendicularly to the longitudinal direction of the electrodes. The use of the comb-like electrodes as shown in FIGS. 27 and 28 ensures flexibility of the electrodes without degrading high-frequency characteristics thereof, and also increases the capacitance between the electrodes and reduces the power emission of the electrodes. Note that the electrodes are preferably formed from a material such as silver, gold, copper or aluminum.

Figure 29:
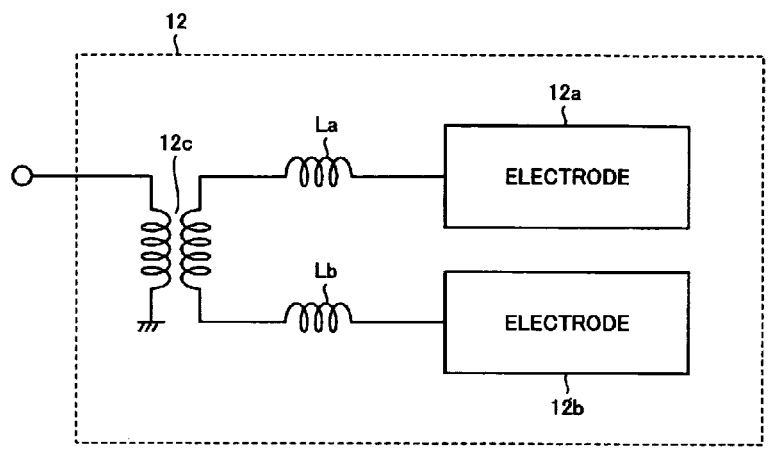
FIG. 29 is a circuit diagram showing another form of the electrode section 12.

FIG. 29 is a circuit diagram showing another form of the electrode section 12. In the biosignal sensing device 2 of the first embodiment in FIG. 2, the oscillating section 11 has a fixed oscillation frequency. Accordingly, the imaginary and real components of the impedance must be corrected so that the impedance can be actually matched between the oscillating section 11 and the electrode section 12. The automatic impedance matching function has been already described in detail with reference to FIGS. 15 to 18. In the example described below, circuit elements are added in order to correct the impedance components separately.

In FIG. 29, coils La, Lb are respectively inserted between the electrodes 12a, 12b and the transformer 12c that serves as an impedance converting means having an isolation function and a function to match a real value of the impedance. As a result, an imaginary component of the impedance is corrected for impedance matching. The coils may be replaced with capacitors.

Figure 30:
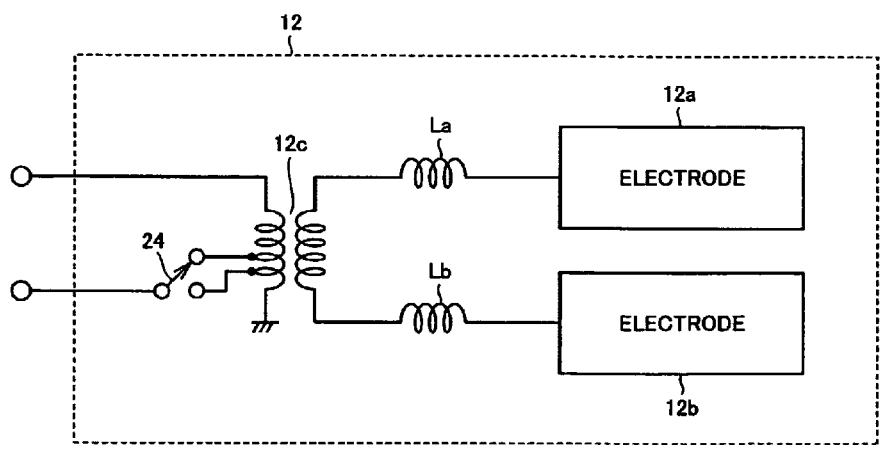
FIG. 30 is a circuit diagram showing still another form of the electrode section 12.

FIG. 30 is a circuit diagram of still another form of the electrode section 12 for impedance correction. In this example, a switch tap 24 is provided on the primary side of the transformer 12c. The turn ratio of the transformer 12c is variable by switching of the switch tap 24, thereby facilitating correction of the real value of the impedance of the electrodes.

Figure 31:
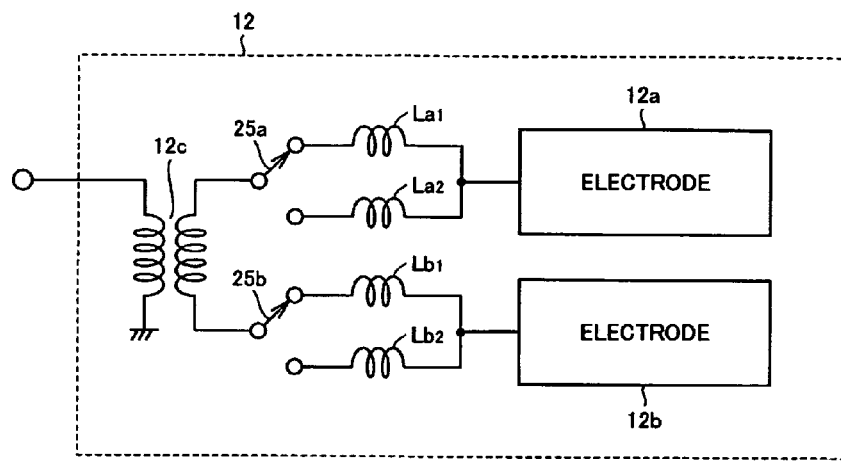
FIG. 31 is a circuit diagram showing yet another form of the electrode section 12.

FIG. 31 is a circuit diagram of yet another form of the electrode section 12 for impedance correction. The example of FIG. 31 includes two coils $La_1$, $La_2$ instead of the coil La and two coils $Lb_1$, $Lb_2$ instead of the coil Lb in the example of FIG. 29, and switches 25a, 25b for selecting coils. This facilitates correction of the imaginary component of the impedance, and thus facilitates impedance matching. The coils may be replaced with capacitors.

Figure 32:
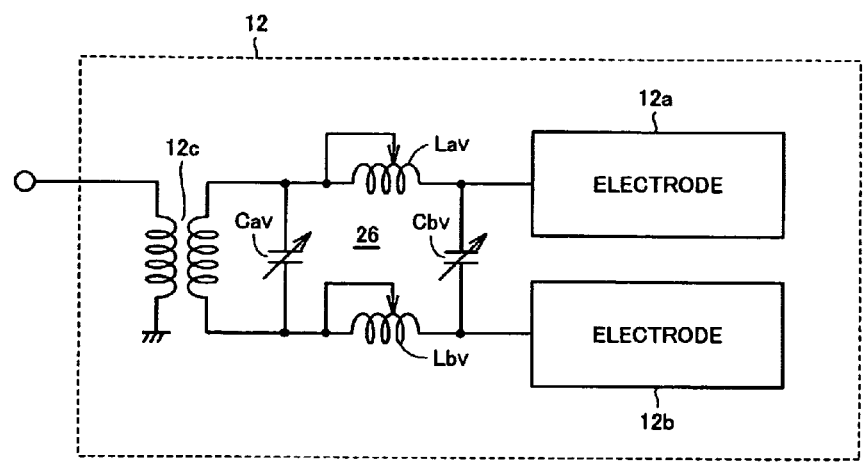
FIG. 32 is a circuit diagram showing a further form of the electrode section 12.

FIG. 32 is a circuit diagram of a further form of the electrode section 12 for impedance correction. The example of FIG. 21 includes a π-type matching circuit 26 instead of the coils La, Lb in the example of FIG. 29.

This matching circuit 26 is a π-type matching circuit modified for a balancing circuit, and includes variable coils Lav, Lbv and variable capacitors Cav, Cbv. The electrode section 12 of this example is capable of realizing impedance matching by adjusting the variable coils Lav, Lbv and the variable capacitors Cav, Cbv of the matching circuit 26. Driving the variable coils Lav, Lbv and the variable capacitors Cav, Cbv with a power source like a motor enables automatic impedance matching as in the embodiment of FIGS. 15 to 18.

Note that, although the π-type matching circuit is used in FIG. 32, a matching circuit of another type such as a T-type matching circuit or an L type matching circuit may alternatively be used.

INDUSTRIAL APPLICABILITY

As has been described above, the biosignal sensing device of the present invention is useful as a biosignal sensing device for accurately sensing a biosignal such as pulse rate and respiration rate without restraining a living body, and is extremely useful particularly when incorporated into a massaging machine because treatment based on the accurately sensed biosignal can be given with inexpensive structure.

The invention claimed is:

1. A biosignal sensing device for sensing a biosignal from a living body as a subject, comprising:
    an oscillating section for supplying a high frequency signal;
    an electrode section including an electrode mounted so that said living body as a subject can be in close proximity to or in contact with said electrode, said electrode being coupled to receive said high frequency signal from said oscillating section;
    a sensing section for sensing a change in impedance that occurs in said electrode receiving said high frequency signal when said living body as a subject is in close proximity to or in contact with said electrode;
    a signal amplifying section having a filter function to extract a signal according a desired biosignal from a signal corresponding to said sensed change in impedance; and
    a signal processing section for producing said desired biosignal from said signal extracted by said signal amplifying section, wherein
    said sensing section produces and supplies a signal indicating a change in reflected-wave level of said high frequency signal corresponding to said change in impedance that occurs in said electrode according to body movement of said living body, and
    a frequency of said high frequency signal supplied from said oscillating section is preset to a value in a region where said reflected-wave level changes at a high rate according to change in said frequency with respect to a region where said reflected-wave level changes at a minimum rate according to change in said frequency,
    wherein said desired biosignal is indicative of a respiration rate.

2. A biosignal sensing device for sensing a biosignal from a living body as a subject, comprising:
    an oscillating section for supplying a high frequency signal;
    an electrode section including an electrode mounted so that said living body as a subject can be in close proximity to or in contact with said electrode, said electrode being coupled to receive said high frequency signal from said oscillating section;
    a sensing section for sensing a change in impedance that occurs in said electrode receiving said high frequency signal when said living body as a subject is in close proximity to or in contact with said electrode;
    a signal amplifying section having a filter function to extract a signal according a desired biosignal from a signal corresponding to said sensed change in impedance; and
    a signal processing section for producing said desired biosignal from said signal extracted by said signal amplifying section, wherein
    said sensing section produces and supplies a signal indicating a change in reflected-wave level of said high frequency signal corresponding to said change in impedance that occurs in said electrode according to body movement of said living body, and
    a frequency of said high frequency signal supplied from said oscillating section is preset to a value in a region where said reflected-wave level changes at a minimum rate according to change in said frequency,
    wherein said desired biosignal is indicative of a pulse rate.

3. The biosignal sensing device according to claim 1 or 2, wherein a frequency of said high frequency signal supplied from said oscillating section is a preset single frequency, said biosignal sensing device further comprising: an automatic impedance matching section for matching impedance produced in said electrode with load impedance of said oscillating section, wherein said automatic impedance matching section senses said change in reflected-wave level according to said change in impedance that occurs in said electrode, and based on said sensed change in reflected-wave level, matches said impedance in said electrode with optimal impedance according to the desired biosignal.

4. The biosignal sensing device according to claim 3, wherein said automatic impedance matching section matches said impedance with a region where said reflected-wave level changes at a high rate according to said change in impedance.

5. The biosignal sensing device according to claim 3, wherein said automatic impedance matching section matches said impedance with a region where said reflected-wave level changes at a minimum rate according to said change in impedance.

6. A biosignal sensing device for sensing a biosignal from a living body as a subject comprising:
    an oscillating section for supplying a high frequency signal;
    an electrode section including an electrode mounted so that said living body as a subject can be in close proximity to or in contact with said electrode, said electrode being coupled to receive said high frequency signal from said oscillating section;

a sensing section for sensing a change in impedance that occurs in said electrode receiving said high frequency signal when said living body as a subject is in close proximity to or in contact with said electrode;

a signal amplifying section having a filter function to extract a signal according a desired biosignal from a signal corresponding to said sensed change in impedance; and a signal processing section for producing said desired biosignal from said signal extracted by said signal amplifying section, wherein said sensing section produces and supplies a signal indicating a change in reflected-wave level of said high frequency signal corresponding to said change in impedance that occurs in said electrode according to body movement of said living body, wherein the frequency of said high frequency signal supplied from said oscillating section is variable, said biosignal sensing device further comprising:

a control section for controlling said oscillating section so as to change said frequency, wherein said sensing section senses said change in reflected-wave level according to said change in frequency, and said control section controls said oscillating section so as to set said variable frequency to a region where said reflected-wave level changes at a high rate according to said change in frequency with respect to a region where said reflected-wave level changes at a minimum rate according to chance in said frequency, wherein said desired biosignal is indicative of a respiration rate.

7. A biosignal sensing device for sensing a biosignal from a living body as a subject comprising:

an oscillating section for supplying a high frequency signal;

an electrode section including an electrode mounted so that said living body as a subject can be in close proximity to or in contact with said electrode, said electrode being coupled to receive said high frequency signal from said oscillating section;

a sensing section for sensing a change in impedance that occurs in said electrode receiving said high frequency signal when said living body as a subject is in close proximity to or in contact with said electrode;

a signal amplifying section having a filter function to extract a signal according a desired biosignal from a signal corresponding to said sensed change in impedance; and a signal processing section for producing said desired biosignal from said signal extracted by said signal amplifying section, wherein said sensing section produces and supplies a signal indicating a change in reflected-wave level of said high frequency signal corresponding to said change in impedance that occurs in said electrode according to body movement of said living body, wherein the frequency of said high frequency signal supplied from said oscillating section is variable;

a control section for controlling said oscillating section so as to change said frequency wherein said sensing section senses said change in reflected-wave level according to said change in frequency and said control section sets said variable frequency to a region where said reflected-wave level changes at a minimum rate according to said change in frequency, wherein said desired biosignal is indicative of a pulse rate.

8. The biosignal sensing device according to claim 6 or 7, comprising said signal amplifying section and said signal processing section for each of a plurality of types of biosignals.

9. The biosignal sensing device according to claim 1, 2, 6 or 7 further comprising a reference signal setting section for determining whether said living body as a subject is properly in close proximity to or in contact with said electrode or not by comparing said signal indicating said change in reflected-wave level with a reference signal of a prescribed level.

10. The biosignal sensing device according to claim 1, 2, 6 or 7 wherein said electrode is a comb-like electrode.

11. The biosignal sensing device according to claim 1, 2, 6 or 7 wherein said electrode section further includes an impedance converting means for realizing impedance matching between said electrode and said sensing section.

12. The biosignal sensing device according to claim 11, wherein said electrode section further includes an impedance matching circuit connected between said impedance converting means and said electrode, for correcting impedance of said electrode for impedance matching.

13. A massaging machine for giving treatment to a user in an automated manner based on a prescribed program, comprising:

a massaging unit for giving treatment to said user;

a biosignal sensing device for sensing a biosignal from said user; and an operation control section for driving said massaging unit according to said prescribed program and said sensed biosignal, wherein said biosignal sensing device including an oscillating section for supplying a light frequency signal, an electrode section including an electrode mounted so that said user can be in close proximity to or in contact with said electrode, said electrode being coupled to receive said high frequency signal from said oscillating section, a sensing section for sensing a change in impedance that occurs in said electrode receiving said high frequency signal when said user is in close proximity to or in contact with said electrode, a signal amplifying section having a filter function to extract a signal according a desired biosignal from a signal corresponding to said sensed change in impedance; and a signal processing section for producing said desired biosignal from said signal extracted by said signal amplifying section, wherein said sensing section produces and supplies a signal indicating a change in reflected-wave level of said high frequency signal corresponding to said change in impedance that occurs in said electrode according to body movement of said user, and a frequency of said high frequency signal supplied from said oscillating section is preset to a value in a region where said reflected-wave level changes at a high rate according to change in said frequency with respect to a region where said reflected wave level changes at a minimum rate according to change in said frequency, wherein said desired biosiqnal is indicative of a respiration rate.

14. A massaging machine for giving treatment to a user in an automated manner based on a prescribed program, comprising:

a massaging unit for giving treatment to said user;

a biosignal sensing device for sensing a biosignal from said user; and an operation control section for driving said massaging unit according to said prescribed program and said sensed biosignal, wherein said biosignal sensing device including an oscillating section for supplying a high frequency signal, an electrode section including an electrode mounted so that said user can be in close proximity to or in contact with said electrode, said electrode being coupled to receive said high frequency signal from said oscillating section, a sensing section for sensing a change in impedance that occurs in said electrode receiving said high frequency signal when said user is in close proximity to or in contact with said electrode, a signal amplifying section having a filter function to extract a signal according a desired biosignal from a signal corresponding to said sensed change in impedance; and a signal processing section for producing said desired biosignal from said signal extracted by said signal amplifying section, wherein said sensing section produces and supplies a signal indicating a change in reflected-wave level of said high frequency signal corresponding to said change in impedance that occurs in said electrode according to body movement of said user, and a frequency of said high frequency signal supplied from said oscillating section is preset to a value in a region where said reflected-wave level changes at a minimum rate according to change in said frequency, wherein said desired biosignal is indicative of said pulse rate.

15. The massaging machine according to claim 13 or 14, wherein a frequency of said high frequency signal supplied from said oscillating section is a preset single frequency, said massaging machine further comprising:

an automatic impedance matching section for matching impedance produced in said electrode with load impedance of said oscillating section, wherein said automatic impedance matching section senses said change in reflected-wave level according to said change in impedance that occurs in said electrode, and based on said sensed change in reflected-wave level, matches said impedance in said electrode with optimal impedance according to said desired biosignal.

16. The massaging machine according to claim 15, wherein said automatic impedance matching section matches said impedance with a region where said reflected-wave level changes at a high rate according to said change in impedance.

17. The massaging machine according to claim 15, wherein said automatic impedance matching section matches said impedance with a region where said reflected-wave level changes at a minimum rate according to said change in impedance.

18. The massaging machine according to claim 13 or 14, further comprising a reference signal setting section for determining whether said user is properly in close proximity to or in contact with said electrode or not by comparing said signal indicating said change in reflected-wave level with a reference signal of a prescribed level.

19. A massaging machine for giving treatment to a user in an automated manner based on a prescribed program, comprising:

a massaging unit for giving treatment to said user;

a biosignal sensing device for sensing a biosignal from said user; and an operation control section for driving said massaging unit according to said prescribed program and said sensed biosignal, wherein said biosignal sensing device including an oscillating section for supplying a high frequency signal, an electrode section including an electrode mounted so that said user can be in close proximity to or in contact with said electrode, said electrode being coupled to receive said high frequency signal from said oscillating section, a sensing section for sensing a change in impedance that occurs in said electrode receiving said high frequency signal when said user is in close proximity to or in contact with said electrode, a signal amplifying section having a filter function to extract a signal according a desired biosignal from a signal corresponding to said sensed change in impedance; and a signal processing section for producing said desired biosignal from said signal extracted by said signal amplifying section, wherein said sensing section produces and supplies a signal indicating a change in reflected-wave level of said high frequency signal corresponding to said change in impedance that occurs in said electrode according to body movement of said user, wherein the frequency of said high frequency signal supplied from said oscillating section is variable, said massaging machine further comprising:

a control section for controlling said oscillating section so as to change said frequency, wherein said sensing section senses said change in reflected-wave level according to said change in frequency, and said control section controls said oscillating section so as to set said variable frequency to a region where said reflected-wave level changes at a high rate according to said change in frequency with respect to a region where said reflected wave level changes at a minimum rate according to change in said frequency, wherein said desired biosignal is indicative of a respiration rate.

20. A massaging machine for giving treatment to a user in an automated manner based on a prescribed program, comprising:

a massaging unit for giving treatment to said user;

a biosignal sensing device for sensing a biosignal from said user;

an operation control section for driving said massaging unit according to said prescribed program and said sensed biosignal, wherein said biosignal sensing device including an oscillating section for supplying a high frequency signal, an electrode section including an electrode mounted so that said user can be in close proximity to or in contact with said electrode, said electrode being coupled to receive said high frequency signal from said oscillating section, a sensing section for sensing a change in impedance that occurs in said electrode receiving said high frequency signal when said user is in close proximity to or in contact with said electrode, a signal amplifying section having a filter function to extract a signal according a desired biosignal from a signal corresponding to said sensed change in impedance; and a signal processing section for producing said desired biosignal from said signal extracted by said signal amplifying section, wherein said sensing section produces and supplies a signal indicating a change in reflected-wave level of said high frequency signal corresponding to said change in impedance that occurs in said electrode according to body movement of said user wherein the frequency of said high frequency signal supplied from said oscillating section is variable, said massaging machine further comprising:

a control section for controlling said oscillating section so as to change said frequency, wherein said sensing section senses said change in reflected-wave level according to said change in frequency, and said control section sets said variable frequency to a region where said reflected-wave level changes at a minimum rate according to change in said frequency, wherein said desired biosignal is indicative of a pulse rate.

21. The massaging machine according to claim 19 or 20, comprising said signal amplifying section and said signal processing section for each of a plurality of types of biosignals.

22. The massaging machine according to claim 19 or 20, further comprising a reference signal setting section for determining whether said user is properly in close proximity to or in contact with said electrode or not by comparing said signal indicating said change in reflected-wave level with a reference signal of a prescribed level.

23. The massaging machine according to claim 13, 14, 19 or 20, wherein said electrode is a comb-like electrode.

24. The massaging machine according to claim 13, 14, 19 or 20, wherein said electrode section further includes an impedance converting means for realizing impedance matching between said electrode and said sensing section.

25. The massaging machine according to claim 24, wherein said electrode section further includes an impedance matching circuit connected between said impedance converting means and said electrode, for correcting impedance of said electrode for impedance matching.

* * * * *